United States Patent
Franzen et al.

(10) Patent No.: US 7,015,471 B2
(45) Date of Patent: Mar. 21, 2006

(54) SURFACE PLASMON RESONANCE SYSTEMS AND METHODS HAVING A VARIABLE CHARGE DENSITY LAYER

(75) Inventors: Stefan Franzen, Apex, NC (US); Scott Brewer, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 267 days.

(21) Appl. No.: 10/669,401

(22) Filed: Sep. 23, 2003

(65) Prior Publication Data
US 2004/0113077 A1    Jun. 17, 2004

Related U.S. Application Data

(60) Provisional application No. 60/413,365, filed on Sep. 25, 2002.

(51) Int. Cl.
*C12Q 1/68* (2006.01)
(52) U.S. Cl. ......................... 250/338.1; 435/4
(58) Field of Classification Search ............ 250/338.1; 435/4, 7.4, 15, 24; 356/335, 336, 338, 339, 356/340; 210/198.2, 502.1, 635, 656
See application file for complete search history.

(56) References Cited

U.S. PATENT DOCUMENTS

| | | |
|---|---|---|
| 2,340,354 A | 2/1944 | Wells |
| 3,119,355 A | 1/1964 | Gawlitza et al. |
| 3,249,741 A | 5/1966 | Mills |
| 4,363,955 A | 12/1982 | Gauthier et al. |
| 4,421,015 A | 12/1983 | Masters et al. |
| 5,223,290 A | 6/1993 | Alden |
| 5,641,640 A | 6/1997 | Hanning .................. 435/7.92 |
| 5,955,729 A | 9/1999 | Nelson et al. .............. 250/282 |
| 5,965,456 A | 10/1999 | Malmqvist et al. .......... 436/514 |
| 6,127,183 A | 10/2000 | Ivarsson et al. ............. 436/34 |
| 6,143,574 A | 11/2000 | Karlsson et al. ............ 436/517 |
| 6,478,939 B1 * | 11/2002 | Lennox et al. ......... 204/403.08 |
| 6,558,193 B1 | 5/2003 | Sawayanagi et al. |
| 6,762,025 B1 | 7/2004 | Cubicciotti et al. |
| 6,770,441 B1 | 8/2004 | Dickinson et al. |
| 6,783,672 B1 | 8/2004 | Tubbs et al. |
| 6,787,647 B1 | 9/2004 | Milne-Edwards et al. |

(Continued)

FOREIGN PATENT DOCUMENTS

WO    WO 99/11992    3/1999

(Continued)

OTHER PUBLICATIONS

Hamberg, I.; Hjortsberg, A.; Granqvist, C.; *Applied Physics Letters* 1982, 40, 362-364.

(Continued)

*Primary Examiner*—Otilia Gabor
(74) *Attorney, Agent, or Firm*—Myers Bigel Sibley & Sajovec

(57) ABSTRACT

A device for detecting the presence of a member of a specific binding pair in a sample includes a substrate and a variable charge density layer having a surface adjacent to the substrate and a surface remote from the substrate. A first member of a specific binding pair is on the surface of the variable charge density layer remote from the substrate. The first member interacts with a second member of the specific binding pair present in a sample. The variable charge density layer has a charge carrier density that can be changed by the application of light and/or an electric field, so that a plasmon band is produced by a reflected light source impinging on the variable charge density layer.

81 Claims, 25 Drawing Sheets

U.S. PATENT DOCUMENTS

| | | | |
|---|---|---|---|
| 6,808,874 B1 | 10/2004 | Griffiths | |
| 2002/0102578 A1 | 8/2002 | Dickinson et al. | |
| 2002/0117659 A1 * | 8/2002 | Lieber et al. | 257/14 |
| 2004/0146863 A1 * | 7/2004 | Pisharody et al. | 435/6 |
| 2004/0186359 A1 * | 9/2004 | Beaudoin et al. | 600/310 |
| 2004/0248282 A1 * | 12/2004 | Sobha et al. | 435/287.2 |
| 2005/0130296 A1 * | 6/2005 | Pisharody et al. | 435/287.2 |

FOREIGN PATENT DOCUMENTS

| | | |
|---|---|---|
| WO | WO 01/58269 | 8/2002 |

OTHER PUBLICATIONS

Hjortsberg, A.; Hamberg, I.; Granqvist, C. *Thin Solid Films* 1982, 90, 323-326.

Szczyrbowski, J.; Dietrich, A.; Hoffman, H. *Physica Status Solidi (a)* 1983, 78 243-252.

Brewer, S. H., Franzen, S., "Optical properties of indium tin oxide and fluorine-doped tioxidesurfaces:correlation of reflectivity, skin depth, and plasmon frequency with conductivity," *Journal of Alloys and Compounds* 338 (2002) 73-79.

Hansen, W. *Journal of the Optical Society of America* 1968, 58 380-390.

Fan, J.; Bachner, F.; Foley, G. *Applied Physics Letters* 1977, 31, 773-775.

Stjerna, B.; Olsson, E.; Granqvist, C. *Journal of Applied Physics* 1994, 76, 3797-3817.

Ulman, A. *Chemical Reviews* 1996, 96, 1533-1554.

Lavrich, D.; Wetterer, S.; Bernasek, S.; Scoles, G. *Journal of Physical Chemistry B*, 1998, 102, 3456-3465.

Yan, C.; Zharnikov, M.; Golzhauser, A.; Grunze, M. *Langmuir* 2000, 16, 6208-6215.

Bain, C.; Biebuyck, H.; Whitesides, G. *Langmuir* 1989, 5 723-727.

Kohli, P.; Blanchard, G. *Langmuir* 2000, 16, 8518-8524.

Seip, C.; Talham, D. *Materials Research Bulletin* 1999, 34 437-445.

Petruska, M.; Ganucci, G.; Talham, D. *Chemistry of Materials* 1998, 10 177-189.

Allara, D.; Nuzzo, R. *Langmuir* 1985, 1, 52-66.

Brewer, S.; Franzen, S; "Indium Tin Oxide Plasma Frequency Dependence on Sheet Resistance and Surface Adlayers Determined by Reflectance FTIR Spectroscopy ", *J. Phys. Chem B*, 2002.

Brewer, S; Brown, D; Franzen, S; "Formation of Thiolate and Phosphonate Adlayers on Indium-tin Oxide: Optical and Electronic Characterization" *Langmuir* 2002, 18, 6857-6865.

Allara, D.; Nuzzo, 1985, 1, 45-52.

SPR—Surface Plasmon Resonance, Surface Science Techniques, An Introduction to SPR-Surface Plasmon Resonance, http://www.uksaf.org/tech/spr.html ; 2002.

Copy of International Search Report for PCT/US2004/014329; mailed Dec. 8, 2004.

Copy of Notification of Transmittal of the International Search Report and the Written Opinion of the International Searching Authority, or the Declaration for PCT/US03/30450 . . . .

* cited by examiner

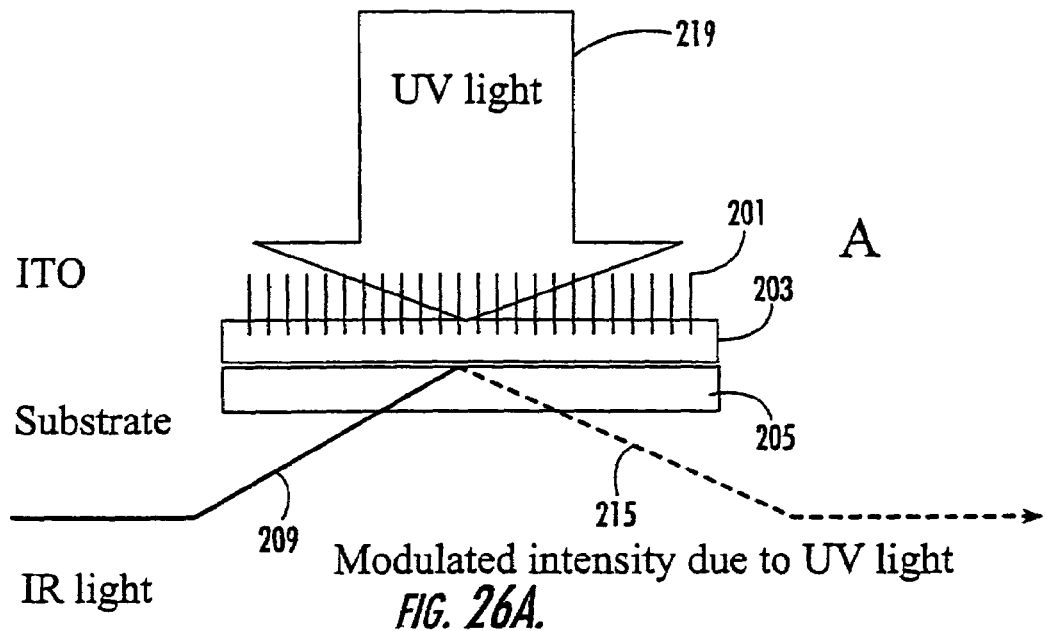
FIG. 26A. Modulated intensity due to UV light
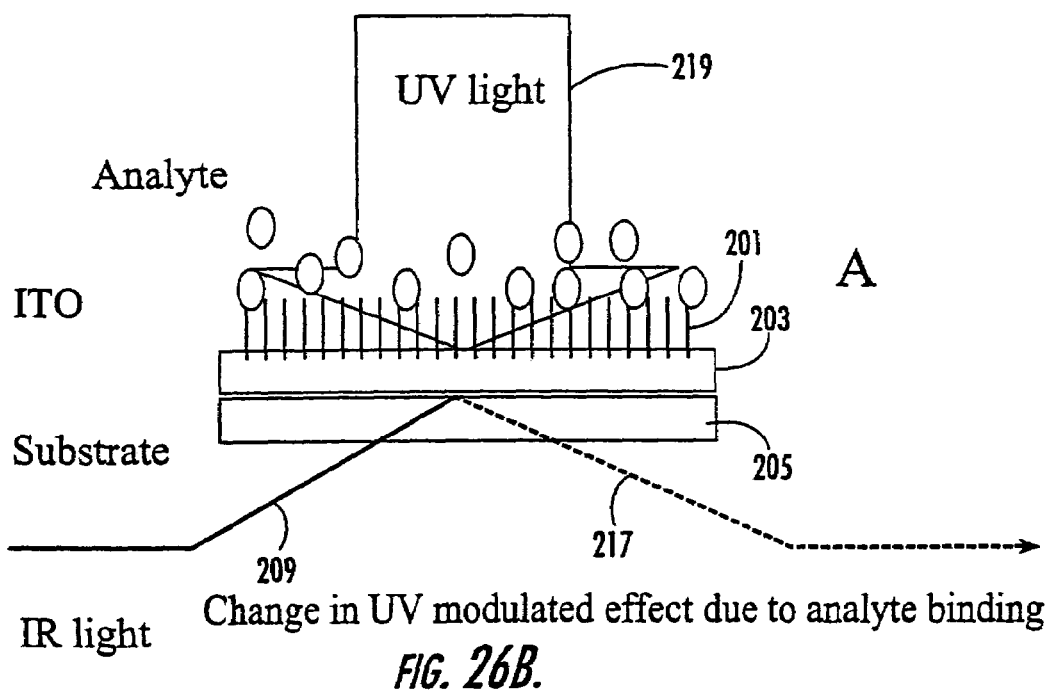
FIG. 26B. Change in UV modulated effect due to analyte binding

SURFACE PLASMON RESONANCE SYSTEMS AND METHODS HAVING A VARIABLE CHARGE DENSITY LAYER

RELATED APPLICATIONS

This application claims priority to U.S. patent application No. 60/413,365 filed Sep. 25, 2002, the disclosure of which is incorporated herein by reference in its entirety.

BACKGROUND OF THE INVENTION

1. Field of the Invention

The present invention relates to methods and systems for detecting a member of a binding pair with surface plasmon resonance.

2. Background

When two media of different refractive index are joined at an interface, light from the medium having a higher refractive index can be partly reflected and partly refracted at the interface. If the angle of incidence is above a certain critical angle, the light is entirely internally reflected and no light is refracted across the interface. At angles above the critical angle for which total reflectance is observed, an electromagnetic field component of the light penetrates a distance on the order of tens of nanometers into the medium of lower refractive index. The electromagnetic field creates an exponentially detenuating evanescent wave.

If the interface between the two media is coated with a thin layer of metal, the intensity of the reflected light is reduced at a specific incident angle due to resonance energy transfer between the electromagnetic field and surface plasmons of the metal. The resonance energy transfer is referred to as surface plasmon resonance. Modifications to the surface of the thin metal film can influence the resonance conditions of the metal.

Surface plasmon resonance can be used as a technique used for the detection of binding to surface layers and can provide information characterizing the properties of a thin film. One example of surface plasmon resonance involves attaching a receptor to a surface of a sensor device. The sensor device includes a thin metal layer to which the receptor is attached. Gold is typically used as the metal layer. One side of the metal layer is contacted with a solution sample containing an analyte of interest. The binding of the analyte with the receptor causes changes in the optical characteristics of the opposite surface of the metal layer. Measuring the changes in optical characteristics can indicate whether binding of the analyte with the receptor occurred.

The absorptive transition that arises at the resonance condition in a metal is commonly referred to as a plasmon resonance band. A metal behaves as a conductor below the plasmon resonance frequency and as an insulator above the plasmon resonance frequency. At the resonance frequency, the metal absorbs electromagnetic radiation.

One theoretical model for describing the intense absorption observed in plasmon resonance is the Drude model. The Drude model is based on an assumption that a metal is a regular three-dimensional array of atoms or ions with a large number of electrons free to move about the whole metal. The "sea of electrons" can be treated as a mass, and the electrostatic attraction of the metal lattice as a spring. The electromagnetic radiation that impinges on the metal surface is a forcing term. The plasmon resonance condition is analogous to the resonance condition that arises for any forced harmonic oscillator. The plasmon resonance frequency is given by Equation 1.

$$\omega_p^2 = \frac{ne^2}{m\varepsilon_0} \quad (1)$$

where n is the free charge carrier concentration, m is the free electron mass, e is the elementary charge of an electron, and $\varepsilon_0$ is the permittivity of vacuum. Wooten, F. *Optical Properties of Solids;* Academic Press, Inc.: Sandiego, 1972.

A metal typically has a relatively high charge carrier concentration that is not altered by the application of light and/or an electric field. At the plasmon resonance frequency, free electrons of a metal will oscillate and absorb energy at a certain angle of incident light. The angle of incident light when surface plasmon resonance occurs is typically referred to as the surface plasmon resonance angle. The surface plasmon resonance of noble metals such as gold and silver are much lower than those of other metals and are accessible by visible and UV spectroscopic approaches. Gold and silver exhibit sensitivity of the surface plasmon frequency and the wave vector. The angular condition for coupling the electromagnetic radiation and surface plasmon as observed in the optical absorption of the plasmon resonance band has been used to detect the binding of surface layers for p-polarized radiation. The change in index of refraction at the surface of the metal changes the angle for maximum plasmon absorption. However, the changes in angle are typically on the order of millidegrees and detection can be difficult. Changes in wavelength observed in gold and silver are typically even more difficult to detect.

Current methods for detecting analytes on surface layers measure the change in index of refraction on a metal surface by measuring the change in the angle of maximum absorption (minimum reflectance). One common implementation of the detection method is the use of a HeNe laser at 632.8 nm in a fixed wavelength measurement. The change in HeNe intensity is proportional to the change in index of refraction of the gold. Current methods detect a change in the surface plasmon resonance angle. For example, U.S. Pat. No. 6,127,183 proposes the detection of changes in the minimum angle of plasmon resonance on gold. U.S. Pat. No. 5,641,640 proposes the detection of changes in the surface plasmon resonance angle to detect analytes bound to the surface of a metal.

Such surface plasmon resonance detection systems may have the sensitivity to detect the binding of an analyte to a submonolayer of surface receptors or binding sites. Hydrogels such as carboxymethylcellulose have been used as an intermediary between the receptors or binding sites to increase the sensitivity of detection. However, the additional material on the surface may present several problems. The direct calibration of the signal with binding events may become more difficult because any effect that swells the hydrogel may give rise to a false signal change. This has led to the use of kinetic assays such as those proposed in U.S. Pat. No. 6,143,574. However, kinetic assays may require that all of the binding sites in the hydrogel be uniformly accessible.

Typical spectra for gold are shown in FIGS. 1A and 1B. FIG. 1A shows the spectrum of reflectivity or light intensity (I) as a function of angle (θ) detected prior to binding on a gold optical layer. There is a sharp decline in intensity at the plasmon resonance angle $\theta_1$. FIG. 1A shows the spectrum of light intensity (I) as a function of angle (θ) after binding occurs between the binding pair on a gold optical layer. The sharp decline in intensity at the plasmon resonance angle $\theta_2$ is observed. The change in angle between $\theta_1$ and $\theta_2$ indicates a change in the optical layer due to binding events.

SUMMARY OF THE INVENTION

In certain embodiments, a device for detecting a member of a specific binding pair in a solution sample is provided. The device includes a substrate and a variable charge density layer having a surface adjacent the substrate and a surface remote from the substrate. A first member of a specific binding pair is on the surface of the variable charge density layer remote from the substrate. The first member interacts with a second member of the specific binding pair present in a sample. The variable charge density layer has a charge carrier density that can be changed by the application of light and/or an electric field, so that a plasmon band is produced by a reflected light source impinging on the variable charge density layer.

In other embodiments, a device for detecting a member of a specific binding pair in a sample includes a substrate and a semiconductor layer having a surface adjacent the substrate and a surface remote from the substrate. A first member of a specific binding pair is on the surface of the semiconductor layer remote from the substrate. The first member interacts with a second member of the specific binding pair present in a sample.

In further embodiments, a system for detecting a member of a specific binding pair in a sample includes a substrate and a variable charge density layer having a surface adjacent the substrate and a surface remote from the substrate. A first member of a specific binding pair is on the surface of the variable charge density layer remote from the substrate. The variable charge density layer has a charge carrier density that can be changed by the application of light and/or an electric field. A first member of a specific binding pair is on the second surface of the variable charge density layer. The first member interacts with a second member of the specific binding pair present in a sample. A means for changing the variable charge density of the variable charge density layer can be used for producing a plasmon band. The plasmon band can be detected from the variable charge density layer by a detection means. Suitable detection mechanisms may include optical detection, for example, in the near infrared region.

In still further embodiments, a method for detecting a member of a specific binding pair in a sample includes altering the charge carrier density of a variable charge density layer in response to a binding event.

In yet other embodiments, a method for detecting a member of a specific binding pair in a sample is provided. A first plasmon band measurement is detected from a reflected light source on an optical layer having a first member of a specific binding pair attached thereto. A sample is placed in contact with the first member of the specific binding pair. A second plasmon band measurement is measured from the reflected light source on the optical layer. If a plasmon frequency shift in the first and second plasmon band measurements is detected to indicate binding, a determination is made that the sample comprises a second member of the specific binding pair.

In still further embodiments, a method for detecting a member of a specific binding pair in a sample includes measuring a first plasmon band measurement from a reflected first light source on an optical layer having a first member of a specific binding pair attached thereto. A sample is placed in contact with the first member of the specific binding pair. A second plasmon band measurement is measured from the first light source on the optical layer. A second light source shines on the optical layer to modulate the first and second plasmon band measurements.

BRIEF DESCRIPTION OF THE DRAWINGS

FIGS. 26A and 26B are schematic drawings of embodiments of the invention using a mid-infrared or near-infrared interferometric spectrometer with a second modulating ultraviolet (UV) light source.

DETAILED DESCRIPTION OF THE INVENTION

Figure 1A:
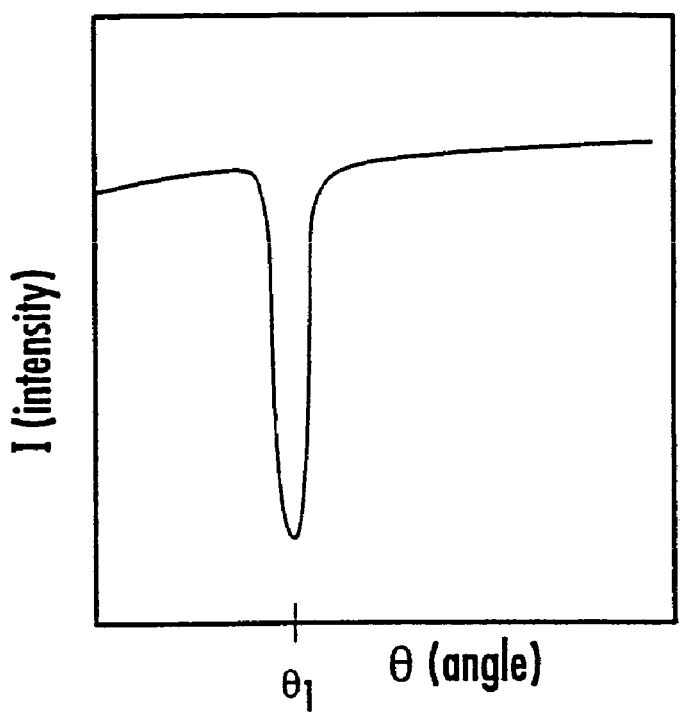
FIGS. 1A and 1B are exemplary plasmon resonance bands on a gold optical layer.

The present invention now will be described more fully hereinafter with reference to the accompanying drawings, in which various embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. In the drawings, the relative sizes of elements may be exaggerated for clarity. Like reference numerals in the drawings denote like members.

When a layer is described as being formed "on" or "adjacent to" another layer or element, the layer may be formed directly on the other layer or element, or other layers may be interposed therebetween. In contrast, when an element is referred to as being "directly on" another element, there are no intervening elements present. The thicknesses of layers or regions may be exaggerated for clarity.

All publications, patent applications, patents, and other references mentioned herein are incorporated by reference in their entirety.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

"Target molecule" as used herein refers to any type of molecule for which detection may be desired, including but not limited to peptides, proteins, nucleic acids, polysaccharides, lipids, lipoproteins, whole cells, etc.

"Binding pair" refers to a pair of molecules, one of which may be a target molecule or probe, which members of said pair of molecules specifically and selectively bind to one another. Examples of suitable binding pairs include, but are not limited to: nucleic acid and nucleic acid; protein or peptide and nucleic acid; protein or peptide and protein or peptide; antigens and antibodies; receptors and ligands, haptens, or polysaccharides, complementary nucleic acids, pharmaceutical compounds, etc. Members of binding pairs are sometimes also referred to as "binders" herein.

The term "nucleic acid" as used herein refers to any nucleic acid, including both DNA and RNA. Nucleic acids of the present invention are typically polynucleic acids; that is, polymers of individual nucleotides that are covalently joined by 3', 5' phosphodiester bonds.

The term "complementary nucleic acid" as used herein refers to any nucleic acid, including oligonucleotide probes, that specifically binds to another nucleic acid to form a hybridized nucleic acid.

The term "probe" as used herein refers to a molecule which specifically binds to another molecule in a binding pair, which probe molecule may be used to determine the presence or absence of the other molecule. Probes may be any member of a binding pair and include, for example, proteins, peptides, natural or synthetic nucleic acids such as DNA or RNA, etc.

The term "sample" as used herein refers to what is applied to or deposited on the optical layer surface. The sample may be derived or obtained from a single source, or derived or obtained from a plurality of sources.

The term "plasmon band" and "plasmon spectrum" are used interchangeably herein to refer to the signal of reflected light from an optical layer received by a detector.

The term "wave number" refers to the number of complete wave cycles that exist in one centimeter (1 cm) of linear space. Wave number is expressed in reciprocal centimeters ($cm^{-1}$).

The term "skin depth" is a property of a substance and is the distance through which incident electromagnetic radiation penetrates.

While the methods and apparatus of the present invention are sometimes explained with respect to analyte and receptor binding pairs herein for purposes of clarity, it is to be understood that the methods and apparatus of the instant invention may be applied to other targets, probes, and other binders.

In certain embodiments, a device for detecting a member of a specific binding pair in a solution sample is provided. The device includes substrate and a variable charge density layer having a surface adjacent the substrate and a surface remote from the substrate. A first member of a specific binding pair is on the surface of the variable charge density layer remote from the substrate. The first member interacts with a second member of the specific binding pair present in a sample. The variable charge density layer has a charge carrier density that can be changed by the application of light and/or an electric field, so that a plasmon band is produced by a reflected light source impinging on the variable charge density layer.

Preferably, the light is polarized such that it has a significant component perpendicular to the surface (also known as p-polarization). The substrate can be transparent and light may pass through the substrate and impinge on the variable charge density layer. The substrate can be nontransparent such that light can impinge on the variable charge density layer from the surface of the variable charge density layer remote from the substrate. Examples of suitable materials for use as a substrate include glass, quartz, infrared transparent non-conducting metals, chalcogenide, SiAl oxides, ZnS, ZnSe, $CaF_2$, $BaF_2$, Ge, Si, and C.

Figure 1B:
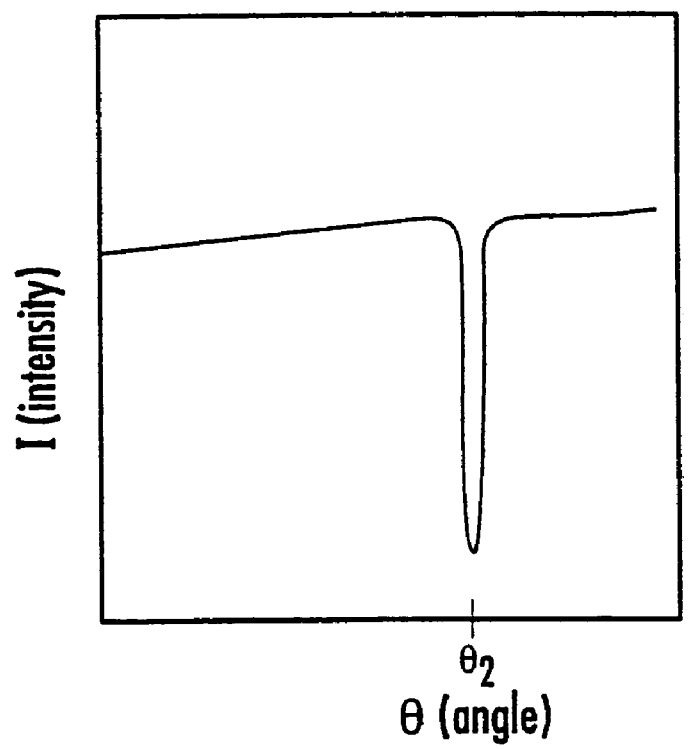

Without wishing to be bound by theory, it is believed that because the charge carrier density of the optical layer can be changed by the application of light and/or an electric field, the resulting plasmon band does not exhibit the characteristic plasmon resonance bands shown in FIGS. 1A and 1B.

Rather, the resulting plasmon band typically exhibits a more complex shape, examples of which are discussed herein.

The example spectra described herein indicate that semiconductors, metal oxides and other optical layers having a charge carrier density that can be changed by the application of light and/or an electric field exhibit a detectable, shallow wavelength dependence of the surface plasmon effect. In contrast, the detection of the surface plasmon resonance effects on gold surfaces is typically a measurement of the change in angle of the absorptive band. The angular changes due to surface plasmon resonance effects on gold may be less sensitive than the changes in reflectivity, frequency, and the maximum of the plasmon resonance band on surfaces according to the present invention. According to embodiments of the present invention, the detection of surface binding events may be carried out using a fixed angle geometry in an FTIR spectrometer. The greatest sensitivity to surface plasmon resonance effects is believed to be in the area of the spectrum closest to the plasmon band maximum. For example, the plasmon band maximum for indium tin oxide (ITO) is in the near-infrared, and it is expected that the greatest sensitivity will be achieved in that region. However, the change in reflectivity between 2500–4000 $cm^{-1}$ appears sufficiently large that surface adlayers may be detected in a common mid-IR FTIR spectrometer by reflectivity. Detection of surface adlayers in the mid-IR region may be a more cost-effective approach to the design of a cell for the detection of binding events.

Suitable optical layer include, metal oxides, non-degenerate semiconductors, degenerate semiconductors, and metal chalcogenides. Such materials may have much smaller numbers of conduction electrons in comparison to conventional gold and silver optical layers. For example, gold and silver have a charge carrier density of about $10^{23}$ electrons/$cm^3$, while semiconductors such as ITO typically have a charge carrier density of about $10^{21}$ electrons/$cm^3$. The plasmon bands observed from noble metals such as gold and silver typically exhibit sharp absorption bands as shown in FIGS. 1A and 1B. The characteristics of a plasmon band from ITO, however, are quite different from those on gold and silver. The observed plasmon bands from ITO exhibit more subtle changes in reflectance intensity as a function of angle rather than the sharp absorption bands of gold or silver. On the other hand, the changes in the plasmon band caused by binding on the surface of optical layers according to the invention may be more sensitive than the angular changes detected in gold or silver. Such changes may include frequency and intensity changes that may be detected at a fixed angle.

Plasmon bands observed from conventional gold optical layers exhibit various other different properties from those observed in optical layers according to embodiments of the invention. For example, the ITO plasmon band maximum is in the near infrared (ca. 9000 $cm^{-1}$ or 1100 nm) instead of 490 nm for gold and 320 nm for silver. Wooten, F. *Optical Properties of Solids;* Academic Press, Inc.: San Diego, 1972. The plasmon band maximum difference may reflect the lower charge carrier density (n) in the metal oxides. Furthermore, ITO is widely used both for its reflecting properties in the mid-infrared and as a heat shield because it is transparent in the visible region of the electromagnetic spectrum. Hamberg, I.; Hjortsberg, A.; Granqvist, C.; *Applied Physics Letters* 1982, 40, 362–364. Hjortsberg, A.; Hamberg, I.; Granqvist, C. *Thin Solid Films* 1982, 90, 323–326. These properties may be typical of materials that are nonconducting in the visible region. ITO, for example, is a degenerate semiconductor and has a band gap of 3.7 eV. Szczyrbowski, J.; Dietrich, A.; Hoffman, H. *Physica Status Solidi (a)* 1983, 78 243–252. The properties of such materials allow methods of surface plasmon resonance detection that may not be possible with the noble metals. The methods described herein are referred to as optical band gap modulated surface plasmon resonance (OBG-SPR). Moreover, since the skin depth of materials according to the invention such as ITO may be much larger than that of gold or silver surface electric fields, the formation of adlayers may have a much larger effect than on the noble metals. The optical properties of ITO and fluorine doped tin oxide are discussed in Brewer, S. H., Franzen, S., "Optical properties of indium tin oxide and fluorine-doped tin oxide surfaces: correlation of reflectivity, skin depth, and plasmon frequency with conductivity," Journal of Alloys and Compounds 338 (2002) 73–79.

In addition, it may be possible to directly detect the infrared spectra of surface layers adsorbed to optical layer materials described herein because the skin depth of ITO and other optical layer materials described herein may be larger than the film thickness. Application of both mid-IR and near-IR in a spectrometer may simultaneously detect the infrared spectrum of the surface bound molecular species and the change in reflectivity or plasmon resonance band.

According to some embodiments of the invention, the plasmon band can have a wave number between about 2,000 $cm^{-1}$ to about 14,000 or 20,000 $cm^{-1}$. The optical layer can include a metal oxide, a degenerate semiconductor, and/or at least one of indium tin oxide, fluorine-doped tin oxide, iridium oxide, ruthenium oxide, cadmium oxide, yttrium oxide, scandium oxide, yttrium tin oxide, and scandium tin oxide. The optical layer can be a conducting metal oxide or metal chalcogenide that is an infrared light reflector and transparent to visible light.

In some embodiments, shining a second light source on the optical layer produces a modulation of a plasmon band measured by the reflected light source impinging upon the optical layer. In other embodiments, the first member of the specific binding pair is a monolayer on the surface of the optical layer and may be essentially free of a polymer. Examples of polymers include hydrogels. The reflected light source can be an infrared polarized light source.

Without wishing to be bound by theory, certain materials such as semiconductors have an associated charge carrier density (n) that may be altered by excitation across the optical band gap. A light source, such as a UV light source, that impinges on the surface of such an optical layer can produce a shift in the plasmon band and a change in the reflectivity of the optical layer. The frequency of the light is preferably greater than the optical band gap, for example, about 1.1 eV for silicon and about 3 eV for ITO, such that the light source has an energy that is higher than the band gap of the optical layer. The modulation of the plasmon bands by a second light source may result in a more sensitive detection methodology for surface plasmon resonance due to an increase in charge carrier density due to promotion across the band gap caused by the light source. More sensitive detection of binding events may be possible by using simultaneous excitation of the optical layer using UV light and the resulting change in electrostatic field at the optical layer surface to observe a modulation of the surface plasmon resonance band or reflectivity. Surface plasmon resonance effects on metal materials such as gold or silver are not typically sensitive enough to detect the binding of an analyte to a submonolayer of surface receptors or binding sites. Thus, the use of hydrogels on the surface (e.g. carboxymethylcellulose) is generally required to enhance to plasmon resonance angle shift such that binding events can be detected. The use of optical layers according to embodiments of the present invention combined with a ultraviolet light source may increase sensitivity of detection and reduce the need for hydrogel.

In other embodiments, a device for detecting a member of a specific binding pair in a sample includes a substrate and a semiconductor layer having a surface adjacent the substrate and a surface remote from the substrate. A first member of a specific binding pair is on the surface of the semiconductor layer remote from the substrate. The first member interacts with a second member of the specific binding pair present in a sample.

In further embodiments, a system for detecting a member of a specific binding pair in a sample includes a substrate and a variable charge density layer having a surface adjacent the substrate and a surface remote from the substrate. A first member of a specific binding pair is on the surface of the variable charge density layer remote from the substrate. The variable charge density layer has a charge carrier density that can be changed by the application of light and/or an electric field. A first member of a specific binding pair is on the second surface of the variable charge density layer. The first member interacts with a second member of the specific binding pair present in a sample. A means for changing the variable charge density of the variable charge density layer can be used for producing a plasmon band. The plasmon band can be detected from the variable charge density layer by a detection means.

Methods according to embodiments of the invention include altering the charge carrier density of a variable charge density layer in response to a binding event. Altering the charge carrier density can include altering the plasmon of the variable charge density layer. A change in the plasmon of the variable charge density layer can be detected, for example, by detecting the plasmon spectrum of reflected light or by detecting a change in the electromagnetic field. The plasmon band of the variable charge density layer may be modulated, for example, by the application of light and/or an electric field.

Figure 2:
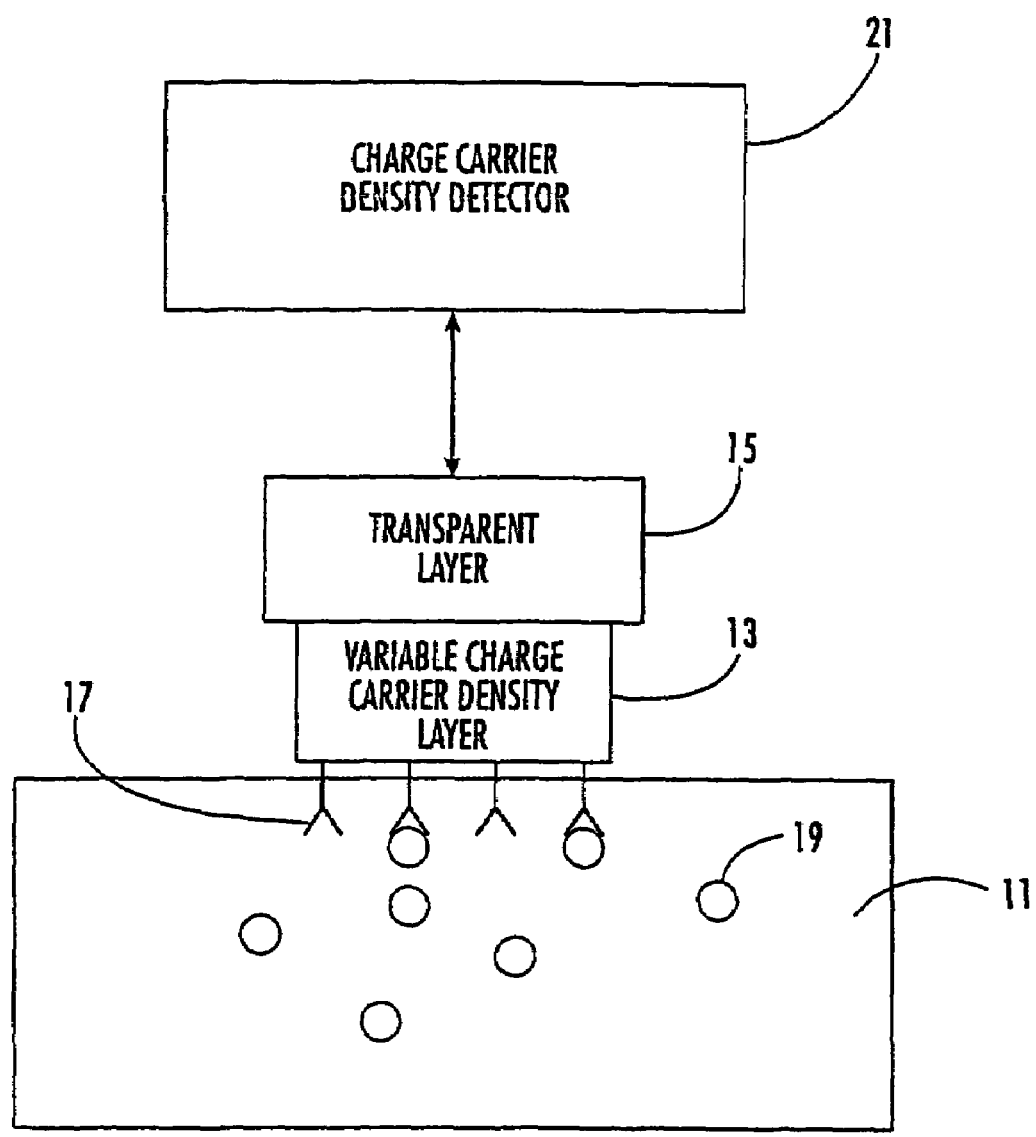
FIG. 2 is a schematic drawing of a surface plasmon resonance detection device.

An exemplary system according to embodiments of the invention is shown in FIG. 2. A variable charge carrier density layer 13 has a surface adjacent a substrate 15. The substrate 15 can be one or more layers of a material including glass and quartz and can provide support for the variable charge carrier density layer 13. A first member 17 of a specific binding pair is on the surface of the variable charge carrier layer 13 that is remote from the substrate 15. A sample 11 including a second member 19 of the specific binding pair is placed in contact with the first member 17. If binding events occur, the charge carrier density of the variable charge carrier density layer 13 changes. The change in charge carrier density is detected by the charge carrier density detector 21. The change in charge carrier density can be detected, for example, by detecting a change in the plasmon of the charge carrier density layer 13. Plasmon changes can include changes in optical characteristics such as changes in the plasmon band produced by light shining on the optical layer.

Figure 3:
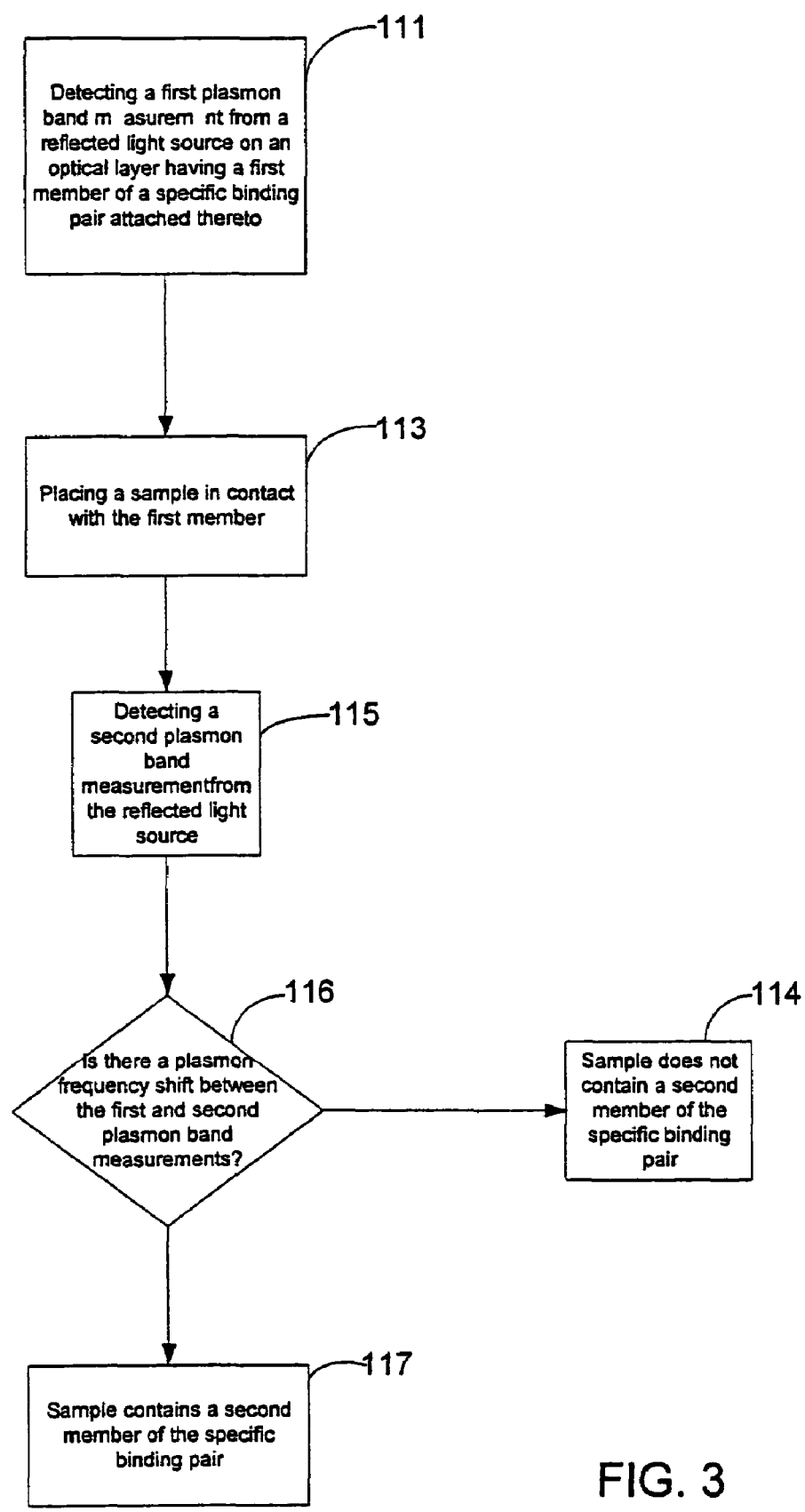
FIG. 3 illustrates the flow of embodiments of operations according to methods according to the invention.

Embodiments of operations according to embodiments of the invention are shown in FIG. 3. A first plasmon band measurement from a reflected light source on an optical layer having a first member of a specific binding pair attached thereto is detected at Block 111. A sample is placed in contact with the first member of the specific binding pair at Block 113. The sample may be a solution sample such as an aqueous solution. A second plasmon band measurement from the reflected light source on the optical layer is detected at Block 115. If a frequency shift between the first and second plasmon band measurements is detected at Block 116, a determination is made that the sample includes a second member of the specific binding pair at Block 117. If no frequency shift between the first and second plasmon band measurements is detected at Block 116, a determination can be made that the sample does not include the second member of the specific binding pair at Block 114.

Methods according to the invention can include shining a second light source on the optical layer during the detection of the first and second plasmon band measurements. The second light source modulates the first and second plasmon band measurements. The second light source may have an energy greater than the band gap of the optical layer. The charge carrier density of the optical layer can be altered by excitation across the optical band gap. Light from a second light source shining on the optical surface can therefore produce a shift in the plasmon band and change the reflectivity of the optical surface. The modulation can result in more sensitive detection. In some embodiments, the sensitivity is increased such that submonolayers of surface receptor interactions may be detected.

Detecting a change in plasmon band frequency can be performed at a fixed angle.

Figure 4:
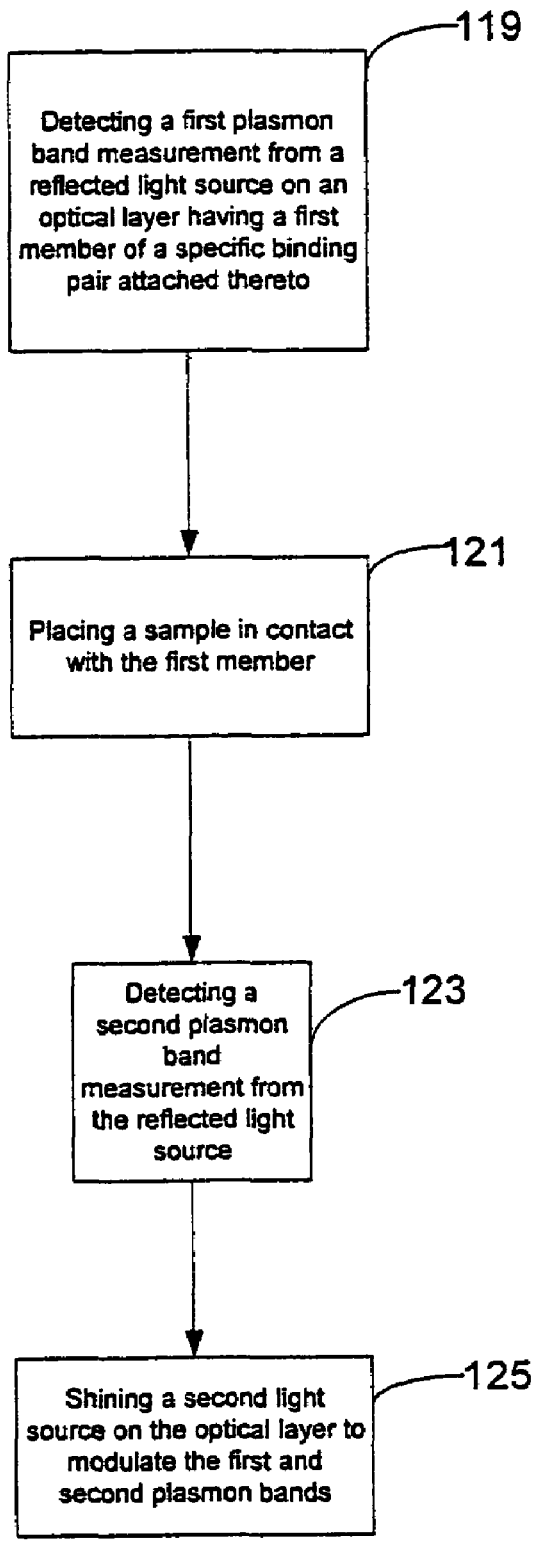
FIG. 4 illustrates the flow of embodiments of operations according to methods according to the invention.

Other embodiments of operations according to the invention are shown in FIG. 4. A first plasmon band measurement is detected from a reflected first light source on an optical layer having a first member of a specific binding pair attached thereto at Block 119. A solution sample including a second member of the specific binding pair is placed in contact with the first member of the specific binding pair at Block 121. A second plasmon band measurement is detected from the reflected first light source on the optical layer at Block 123. A second light source is shined on the optical layer to modulate the first and second plasmon band measurements Block 125. If a plasmon frequency shift in the first and second plasmon band measurements is detected to indicate binding, it may be determined that the sample includes a second member of the specific binding pair.

Figure 5A:
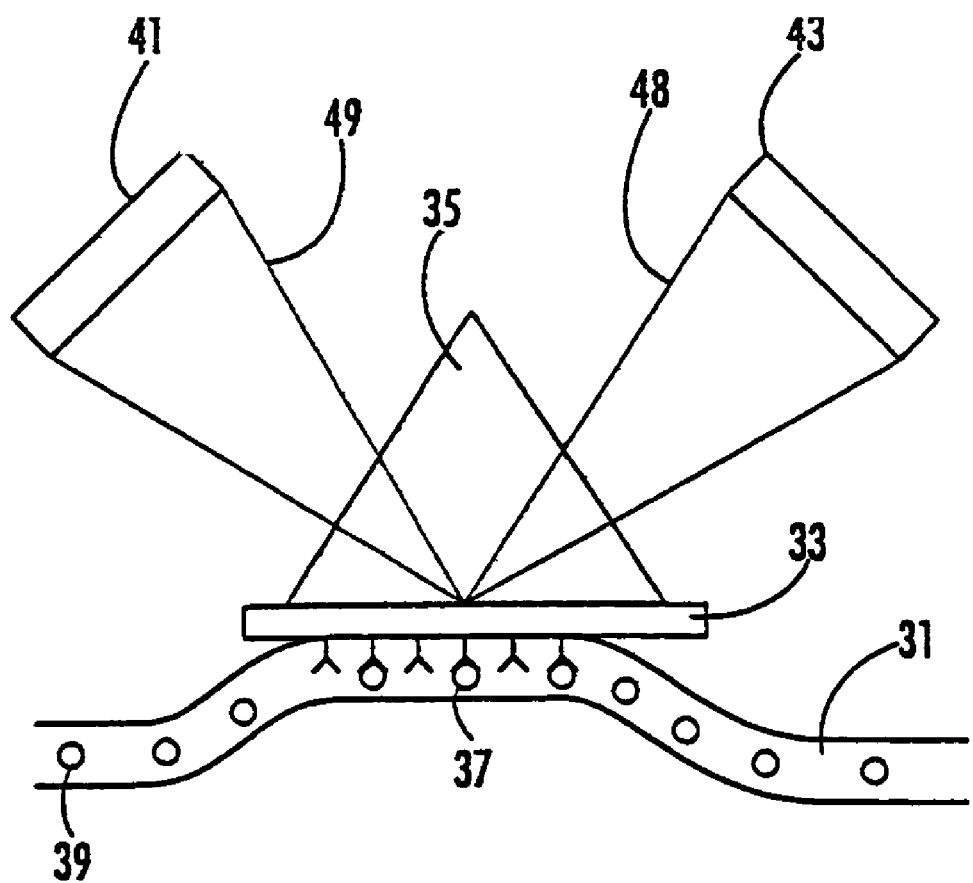
FIG. 5A illustrates a schematic drawing of an exemplary surface plasmon resonance detection device according to embodiments of the invention according to the Kretchmann configuration.

An exemplary system according to embodiments of the invention is shown in FIG. 5A. The system includes a substrate 35 on an optical layer 33. The substrate 35 shown is a prism. The optical layer can be a semiconductor, a degenerate semiconductor, a metal oxide, or a material having a charge carrier density that can be changed by the application of light and/or an electric field. Examples of optical layers include indium tin oxide, fluorine-doped tin oxide, iridium oxide, ruthenium oxide, cadmium oxide, yttrium oxide, scandium oxide, yttrium tin oxide, and scandium tin oxide.

A light source 41 shines an impinging light signal 49 onto the optical layer 33. A detector 43 detects the reflected light signal 48. The impinging light signal 49 interacts with the optical layer 33 such that the reflected light signal 48 has a spectrum that is indicative of the surface plasmon properties of the optical layer 33. A first plasmon band measurement can be recorded from the reflected light signal 48. Examples of plasmon bands are discussed herein.

The optical layer 33 has a first member 37 of a specific binding pair attached thereto. A flow channel 31 contains a solution sample that includes the second member 39 of the specific binding pair. When binding between the first and second members 37, 39 of the specific binding pair occurs on the bottom surface of the optical layer 33, the optical properties of the optical layer 33 change. Optical changes alter the reflected light signal 48 and change the resulting plasmon band detected by the detector 43. Examples of such changes are discussed herein. The system shown in FIG. 5A is similar to a configuration commonly referred to as the Kretchmann configuration used for surface plasmon resonance detection on gold surfaces.

Figure 5B:
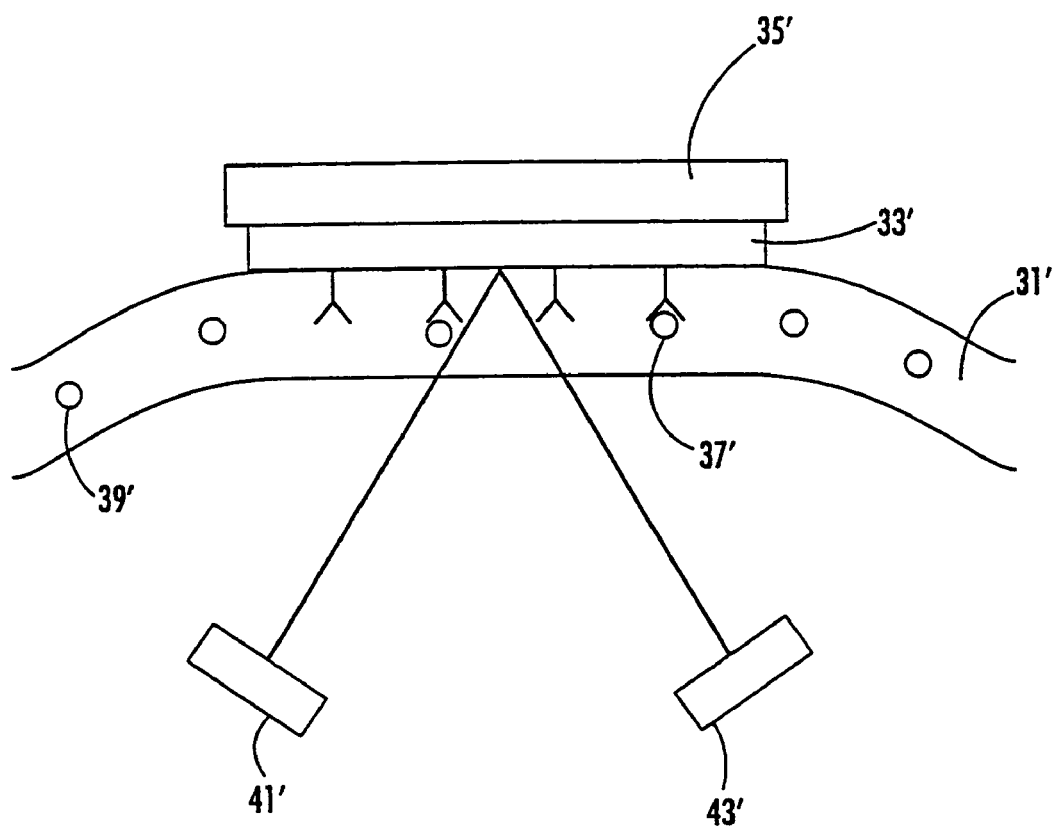
FIG. 5B illustrates a schematic drawing of an exemplary surface plasmon resonance detection device according to embodiments of the invention.

An alternative exemplary system according to embodiments of the invention is shown in FIG. 5B. The system has a substrate 35' on an optical layer 33'. The optical layer can be a semiconductor, a degenerate semiconductor, a metal oxide, or a material having a charge carrier density that can be changed by the application of light and/or an electric field. The optical layer 33' has a first member 37' of a specific binding pair attached thereto. A flow channel 31' contains a solution sample that includes the second member 39' of the specific binding pair. A light source 41' shines an impinging light signal 49' onto the optical layer 33' on the surface of the optical layer 33' to which the first member 37' of the specific binding pair is attached. A detector 43' detects the reflected light signal 48'. The light source does not pass through the substrate 35'. Therefore, the substrate 35' may be transparent or nontransparent. A first plasmon band measurement can be recorded from the reflected light signal 48'. When binding between the first and second members 37', 39' of the specific binding pair occurs on the bottom surface of the optical layer 33', the optical properties of the optical layer 33' change and are detected in the resulting reflected light signal 48'.

Theoretical Models

The following theoretical models are provided for added clarity to illustrate embodiments of the present invention, and should not be construed as limiting thereof.

Drude Free-Electron Model. The Drude free-electron model describes the dielectric function of a material by the plasmon frequency and electronic scattering time as shown in Equation 2:

$$\varepsilon(\omega) = \varepsilon_\infty - \omega_p^2 \frac{1}{\omega^2 + \frac{i\omega}{\tau}} \qquad (2)$$

where $\varepsilon_\infty$ is the high-frequency dielectric constant, $\omega_p$ is the plasmon frequency, $\omega$ is the frequency and $\tau$ is the electronic scattering time. The plasmon frequency is defined in Equation 3:

$$\omega_p^2 = \frac{ne^2}{m\varepsilon_0} \qquad (3)$$

where n is the free charge carrier concentration and m is the free electron mass. The electronic scattering time is calculated from the Hall mobility by (Equation 4):

$$\mu = \frac{e\tau}{m} \qquad (4)$$

where $\mu$ is the Hall mobility. Equation 5 relates the dielectric function to the complex refractive index of the material:

$$\varepsilon(\omega)^{1/2} = N(\omega) = n(\omega) + ik(\omega) \qquad (5)$$

where N is the complex refractive index, n is the real, in-phase, dispersive component and k is the imaginary, out-of-phase, absorptive component of the refractive index. This complex refractive index, along with angle of incidence is used by the Fresnel equations of reflection for a two-phase (single dielectric interface) or three-phase system to model the reflectance of the material for p-polarized radiation. The above equations are further discussed in Wooten, F. *Optical Properties of Solids;* Academic Press, Inc.: San Diego, 1972.

Two-Phase Fresnel Equations for Reflectance. The two-phase Fresnel equations model the reflectance for a single dielectric interface. For instance, these equations model the air/ITO interface where the refractive of index of ITO is complex (n and k components determined from the Drude free-electron model) and the refractive index of air (vacuum) is not complex (only a real component) and taken to be 1 (n=1, k=0). The ratios of the amplitudes of the reflected and incident light for p- and s-polarized radiation for a single dielectric interface is shown in Eqns. 6–8:

$$r_p = \frac{-N\cos\theta + \cos\varphi}{N\cos\theta + \cos\varphi} \qquad (6)$$

$$r_s = \frac{\cos\theta - N\cos\varphi}{\cos\theta + N\cos\varphi} \qquad (7)$$

where $$\cos\varphi = \left(1 - \frac{\sin^2\theta}{N^2}\right)^{\frac{1}{2}} \qquad (8)$$

In these equations, r is the amplitude of the reflected light (relative to incident light amplitude), s or p represent s- or p-polarization, N is the complex refractive index of the material, $\theta$ is the angle of incidence relative to the surface normal, and $\phi$ is the complex angle between the refracted light to the surface normal. Then the power reflectivity for s- or p-polarization is shown in Equation 9 and 10:

$$R_s = |r_s|^2 \qquad (9)$$

$$R_p = |r_p|^2 \qquad (10)$$

where $R_s$ and $R_p$ are the power reflectivity for s- and p-polarization, respectively. Equations 6–10 are further discussed in Fowles, G. *Introduction to Modem Optics;* Second ed.; Dover Publications, Inc.: New York, 1989.

Three-Phase Fresnel Equations for Reflectance. The three-phase Fresnel equations of reflectance models a system composed of two dielectric interfaces. The system used in this analysis is air/ITO/glass, where the glass is the substrate on which the ITO thin film is deposited. The refractive index of air is again taken to only having a real component (n=1, k=0) and the complex dielectric function of ITO is determined from the Drude free-electron model. Literature values for the complex refractive index in the near-IR region for silicon dioxide (glass) were used. The three-phase model takes into account the decay in the magnitude of the electric field through the ITO and the refraction of the light through this thin film before the radiation impinges on the ITO/glass interface. The general form of the ratio of the reflected and incident radiation for a three-phase model of the Fresnel equation is shown in Equation 11:

$$r_p = \frac{r_{p12} + r_{p23}e^{2i\beta}}{1 + r_{p12}r_{p23}e^{2i\beta}} \quad (11)$$

where r is the amplitude of reflected radiation, p refers to p-polarization, the numerical subscripts (1, 2, 3) refer to the three phases (air, ITO, glass) respectively. $\beta$ is defined in Equation 12:

$$\beta = 2\pi\left(\frac{h}{\lambda}\right)N_j\cos\Theta_j \quad (12)$$

where h is the thickness of layer j (taken to be 170 nm for ITO), $\lambda$ is the wavelength of radiation, N is the complex index of refraction (Equation 5) of layer j, and $\Theta$ is the angle relative to the surface normal in layer j. The general form of the two-phase Fresnel equations needed to determine $r_{p12}$ and $r_{p23}$ is defined in Equation 13:

$$r_{pjk} = \frac{N_j\cos\Theta_j - N_k\cos\Theta_k}{N_j\cos\Theta_j + N_k\cos\Theta_k} \quad (13)$$

where the subscripts j and k refer to the $j^{th}$ and $k^{th}$ phase of the model. $\Theta_k$ can be determined from Equation 14:

$$\cos\Theta_k = \left(1 - \frac{\sin^2\Theta_j}{N_k^2}\right)^{1/2} \quad (14)$$

where $\Theta_k$ is the angle in phase k relative to the surface normal. The power reflectivity or calculated reflectance, $R_p$, for p-polarized radiation is defined in Equation 9. Equations 11–14 are further discussed in Hansen, W. *Journal of the Optical Society of America* 1968, 58 380–390.

The following Examples are provided to illustrate embodiments of the present invention, and should not be construed as limiting thereof.

EXAMPLE 1

Plasmon Resonance Phenomenon in Metal Oxides

Example 1 illustrates the optical properties of indium tin oxide (ITO) and fluorine-doped tin oxide (SFO) thin films.

Variable angle reflectance Fourier Transform Infrared Spectroscopy (FTIR) was used to investigate the optical properties of ITO and SFO thin films in the mid- and near-infrared (IR) spectral regions. The reflectance data was used to determine the plasmon frequency, the electronic scattering time, and the high frequency dielectric constant using the Drude free-electron model and the Fresnel equations for reflection. The plasmon frequency and the electronic scattering time were found to vary with the sheet resistance of ITO for p-polarized radiation. The observed plasmon frequency also depended on the incident angle. This was consistent with predictions according to the Fresnel equations. Both the plasmon frequency and electronic scattering time of SFO thin films were found to be lower than any of the ITO thin films studied.

Materials and Methods

ITO and SFO Electrodes. Indium tin oxide (ITO) electrodes were received from Delta Technologies, Limited, Stillwater, Minn., U.S.A. The ITO electrodes were composed of 90% indium oxide and 10% tin oxide, had a nominal thickness of 1,500 Å, and a sheet resistance of 7–14 $\Omega/\square$. The substrate for the ITO electrodes was polished float (soda-lime) glass or fused quartz. The fluorine-doped tin oxide (SFO) electrodes were obtained from PPG Industries, Inc, Pittsburgh, Pa., U.S.A., and had a sheet resistance of 55–56 $\Omega/\square$, while the gold electrodes were obtained from Evaporated Metal Films, Inc., Ithaca, N.Y., U.S.A. The ITO and SFO electrodes were cleaned via 20 minutes of $UV/O_3$ (UVO-cleaner (UVO-60), model number 42, Jelight Company, Inc., Irvine Calif., U.S.A.) to yield a clean hydrophilic surface as determined by water contact angle measurements made using a NRL C.A. Goniometer from Rame-Hart, Inc., Mountain Lakes, N.J., U.S.A., model 100–00. The sheet resistances of these electrodes were measured with a 4-point probe consisting of a SIGNATONE™ D27M probe station from Signatone Corporation, Gilroy, Calif., U.S.A.; a KEITHLEY™ 224 programmable current source from Keithley Instruments, Cleveland, Ohio, U.S.A; and a 3456A digital voltmeter from Hewlett Packard, Palo Alto, Calif., U.S.A.

Reflectance FTIR Spectroscopy. The variable angle reflectance FTIR spectra were recorded using a Spectra-Tech variable angle reflectance attachment (Model 500) in a BRUKER™ IFS v/s spectrometer from Bruker Optics, Billerica, Mass., U.S.A. The angle of incidence ranged from 40–80 degrees. An infrared polarizer was used to obtain s-(horizontal) or p-(vertical) polarized light. A ratio of the single beam spectra of bare ITO electrodes, SFO electrodes, or glass to a single beam spectrum of a gold electrode was performed to obtain the reflectance spectra of ITO, SFO, or glass. A GLOBAR™ source (KANTHAL GLOBAR, Niagara Falls, N.Y.), KBr beamsplitter, and liquid cooled helium photoconductor (boron doped silicon) was used in spectral range 400–4000 $cm^{-1}$, and a tungsten source, quartz beamsplitter, and liquid nitrogen cooled InSb detector was used in the spectral range 2500–15,000 $cm^{-1}$. All IR spectra were the result of the average of 512 scans at a resolution of 2 $cm^{-1}$ and were recorded at room temperature under vacuum.

Reflectance FTIR Spectra.

Figure 6:
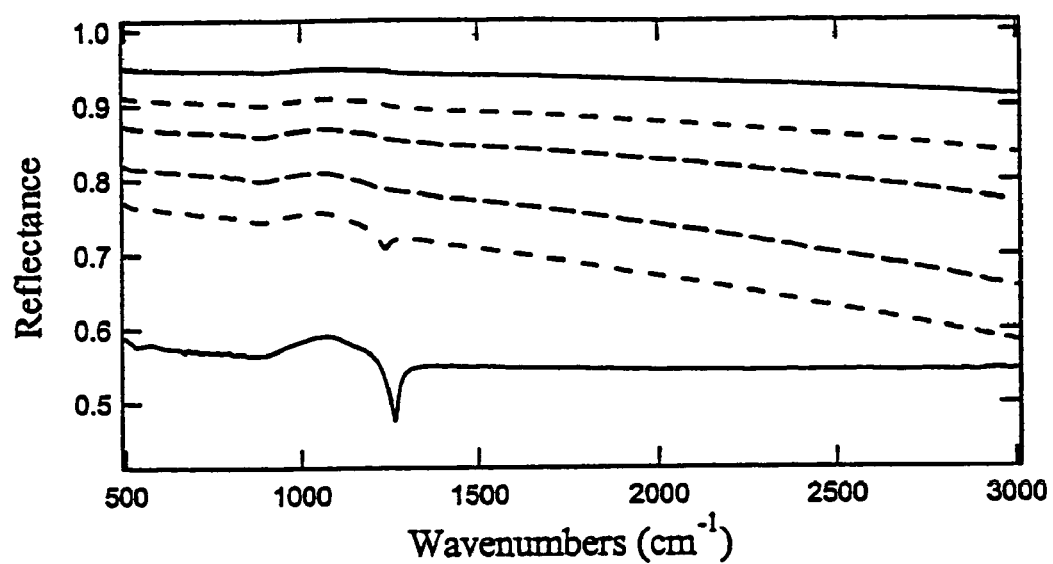
FIG. 6 is the reflectance spectra of indium tin oxide (ITO) deposited on a soda-lime glass substrate.

FIG. 6 shows the reflectance spectra of ITO with a sheet resistance of 13.4 $\Omega/\square$ deposited on a soda-lime glass substrate in the mid-IR with a variety of incident angles and with s- and p-polarized radiation. The top three spectra shown are s-polarized IR radiation and the bottom three spectra are p-polarized IR radiation. The spectra correspond to incident angles of 40 (- - -), 60 (-- -- --), and 80 (solid) degrees. The reflectance decreases for p-polarized radiation and increases for s-polarized radiation as the incident angle increases throughout this region. The general decrease in the reflectance as the wavenumber increases is observed because the region shown is below the plasmon frequency. Therefore, as the wavenumber increases, the reflectance decreases the due to the onset of the plasmon absorptive frequency. This region is generally highly reflective as predicted by the Drude free-electron model. The Fresnel equations for reflection and the Drude free-electron model also show these observed trends with polarization and incident angle theoretically. The modes observed at 1048 and 1256 $cm^{-1}$ in the p-polarized spectra correspond to the transverse and longitudinal optical components of the Si—O—Si vibration. The position of these bands shift depending on the substrate substrate used (soda-lime glass or quartz) and hence can be used to determine the substrate identity.

Figure 7A:
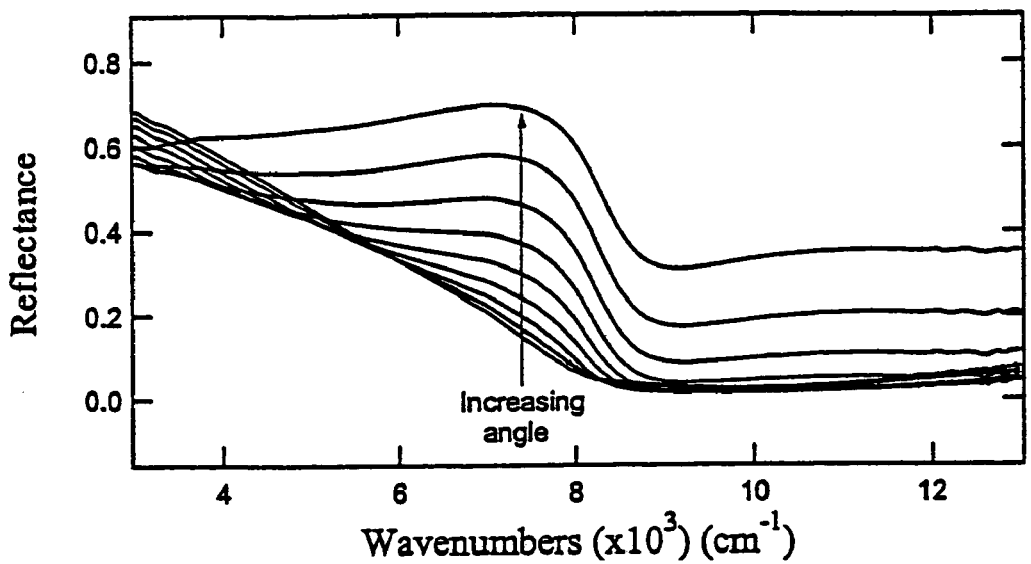
FIGS. 7A and 7B are variable angle reflectance FTIR spectra of a thin film of ITO on a glass substrate.
Figure 7B:
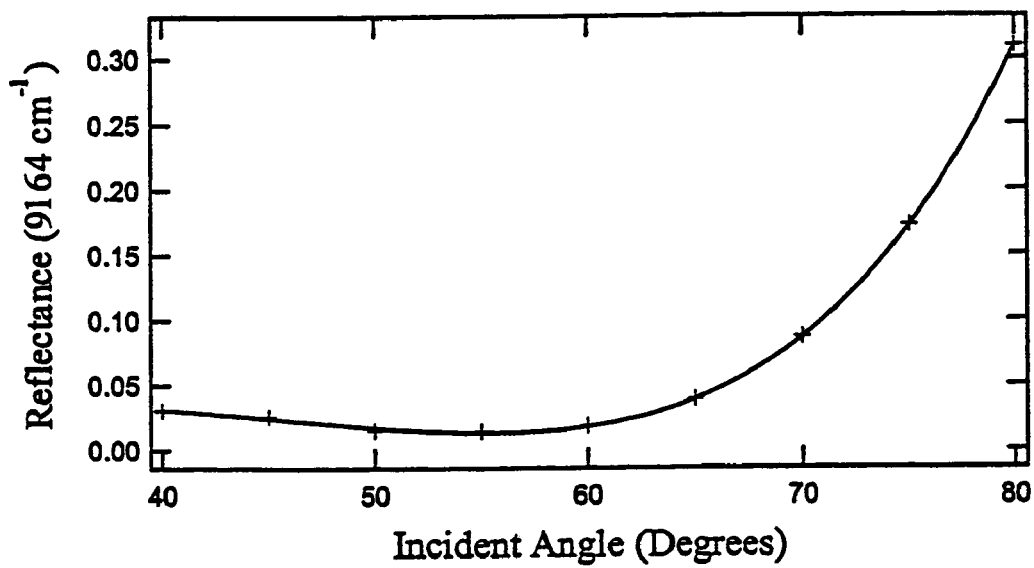

FIGS. 7A and 7B shows the experimental variable angle reflectance FTIR spectra of a thin film of an indium tin oxide (ITO) on a glass substrate in the near-IR region with a sheet resistance of 13.8 $\Omega/\square$. FIG. 7A shows an FTIR spectrum for incident angles ranging from 40 to 80 degrees with p-polarized radiation (air/ITO sampling geometry). FIG. 7B is a plot of the measured reflectance at 9164 cm$^{-1}$ of ITO as a function of incident angle for p-polarized radiation. The measured reflectance was referenced to a gold surface. The angles of incidence were varied between 40–80 degrees relative to the normal using p-polarized IR radiation.

Generally, the reflectance spectra of ITO shown in FIGS. 7A and 7B show relatively high reflectance below about 7500 cm$^{-1}$ and then the reflectance drops substantially. This sharp change in the reflectivity of the ITO is due to the plasmon frequency (as defined in the Drude free-electron model) of the material. The plasmon frequency is characterized by a sharp decrease in the measured reflectance of a material. Therefore, ITO is reflective below the plasmon frequency and transparent at higher energy. However the reflectance and transmittance of the material is dependent on the angle at which the radiation impinges on the material and the polarization of the radiation as shown in FIG. 6. The observed value of the plasmon frequency shifted to lower energy as the incident angle decreased. The position of the observed plasmon frequency did not change with varying angles of incidence for s-polarized radiation as expected by the Fresnel equations for reflection (data not shown). FIG. 7B shows the angle dependence of the reflection of an ITO thin film (13.8 $\Omega/\square$) for p-polarized radiation at 9164 cm$^{-1}$. This plot shows a minimum in the experimental reflectance of ITO, as expected from the Fresnel equations of reflection (data not shown), at about 55 degrees.

Figure 8A:
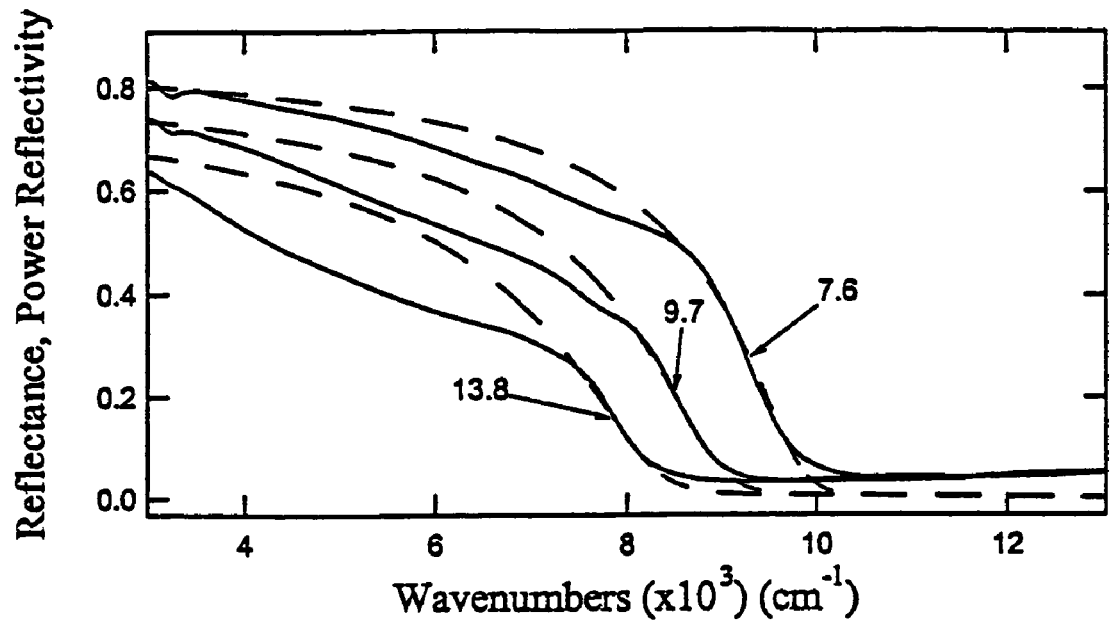
FIGS. 8A and 8B are reflectance FTIR spectra in the region of the plasmon frequency for ITO thin films of different resistances.
Figure 8B:
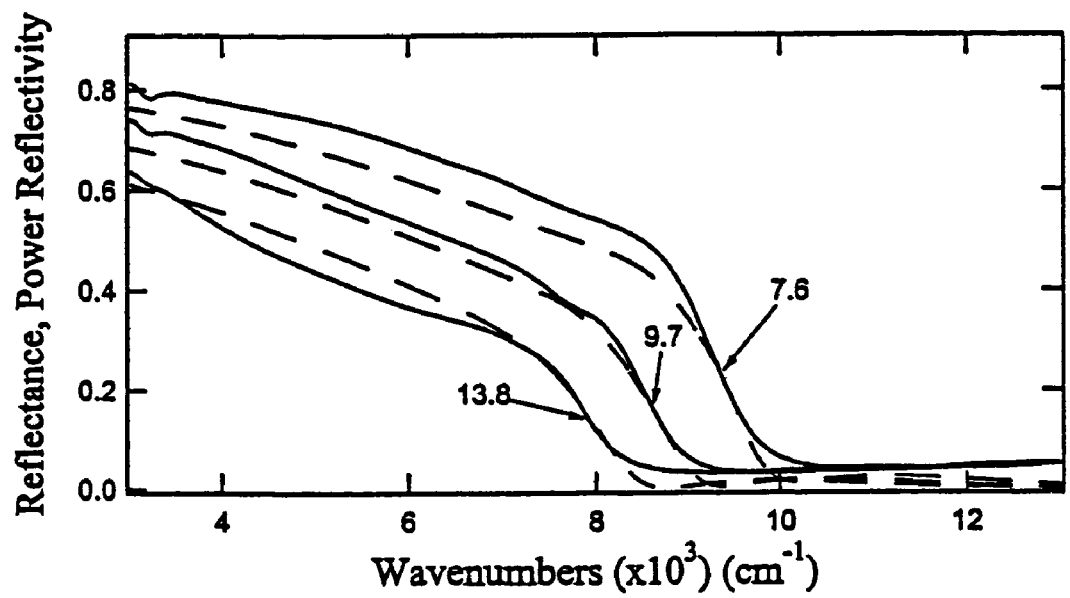

FIGS. 8A and 8B shows the experimental reflectance FTIR spectra in the region of the plasmon frequency for ITO thin films of three different resistances (7.6, 9.7, and 13.8 $\Omega/\square$) recorded at an incident angle of 60 degrees with p-polarized radiation. FIG. 8A also shows the calculated reflectance spectra obtained from the Drude free-electron model and the Fresnel equations for a single dielectric interface (two-phase, air/ITO). FIG. 8B shows the calculated reflectance spectra obtained from the Drude free-electron model and the Fresnel equations for a three-phase (air/ITO/glass). The experimental spectra are shown in solid lines, and the calculated spectra are shown in dashed lines. FIGS. 8A and 8B illustrate that the observed plasmon frequency of ITO is a function of sheet resistance. A red shift in the observed plasmon frequency was observed as the sheet resistance of the metal oxide electrode decreased. The fitted parameters for the Drude free-electron model for these ITO electrodes are listed in Table 1 and 2 using a constant value of 3.8 for the high frequency dielectric constant using the two-phase and three-phase Fresnel equations for reflection, respectively. The values in Table 1 and 2 demonstrate that both the plasmon frequency and the electronic relaxation time decreased as the sheet resistance of the ITO electrode increased. The value of the plasmon frequency ($\omega_p$) is dependent on the charge carrier density (n) and the effective electron mass (m) of the ITO thin film as defined by the Drude free-electron model defined in Equation 3. The value of the plasmon frequency affects the observed sharp decrease in reflectance, while the electronic scattering time affects the curvature of the reflectance spectrum near the observed plasmon frequency. The two parameters of plasmon frequency, the charge carrier density and effective electron mass, are coupled and cannot be individually determined in these experiments. The Drude free-electron model and the Fresnel equations of reflection accurately model the region of the reflectance spectra near the plasmon frequency. However the two-phase model calculates an overall higher absolute reflectance than experimentally observed at wavenumbers lower in energy than the plasmon frequency. The three-phase Fresnel equations of reflection more accurately fit the experimental reflectance of the different ITO samples in the entire near-IR region studied. Therefore, the shifts in the observed plasmon frequency and curvature of the experimental reflectance spectra of ITO thin films with varying sheet resistances were successfully calculated using these theoretical models. The two- or three-phase Fresnel equations of reflection calculated plasmon frequencies that differed by ~100–250 cm$^{-1}$ different while the electronic scattering times were ~5–6 ($\times 10^{-16}$) s higher using the three-phase modeled compared to the two-phase model.

TABLE 1

| Sheet Resistance ($\Omega/\square$) | Electronic Scattering Time ($\tau$) ($10^{-15}$ s) | Plasmon Frequency ($\omega_p$) (cm$^{-1}$) |
|---|---|---|
| 7.6 | 3.8 | 17,200 |
| 9.7 | 3.0 | 15,800 |
| 13.8 | 2.5 | 14,650 |

The electronic scattering time and plasmon frequency of three different ITO electrodes with different sheet resistances as determined from fitting the experimental reflectance data using the Drude free-electron model with a constant value of 3.8 for the high frequency dielectric value to determine the dielectric function of the ITO thin film and the Fresnel equations of reflection for a single dielectric interface (two-phase (air/ITO) model).

TABLE 2

| Sheet Resistance ($\Omega/\square$) | Electronic Scattering Time ($\tau$) ($10^{-15}$ s) | Plasmon Frequency ($\omega_p$) (cm$^{-1}$) |
|---|---|---|
| 7.6 | 4.4 | 17,100 |
| 9.7 | 3.5 | 15,900 |
| 13.8 | 3.0 | 14,900 |

The electronic scattering time and plasmon frequency of three different ITO electrodes with different sheet resistances as determined from fitting the experimental reflectance data using the Drude free-electron model with a constant value of 3.8 for the high frequency dielectric value to determine the dielectric function of the ITO thin film and the three-phase (air/ITO/glass) Fresnel equations for reflection.

Figure 9:
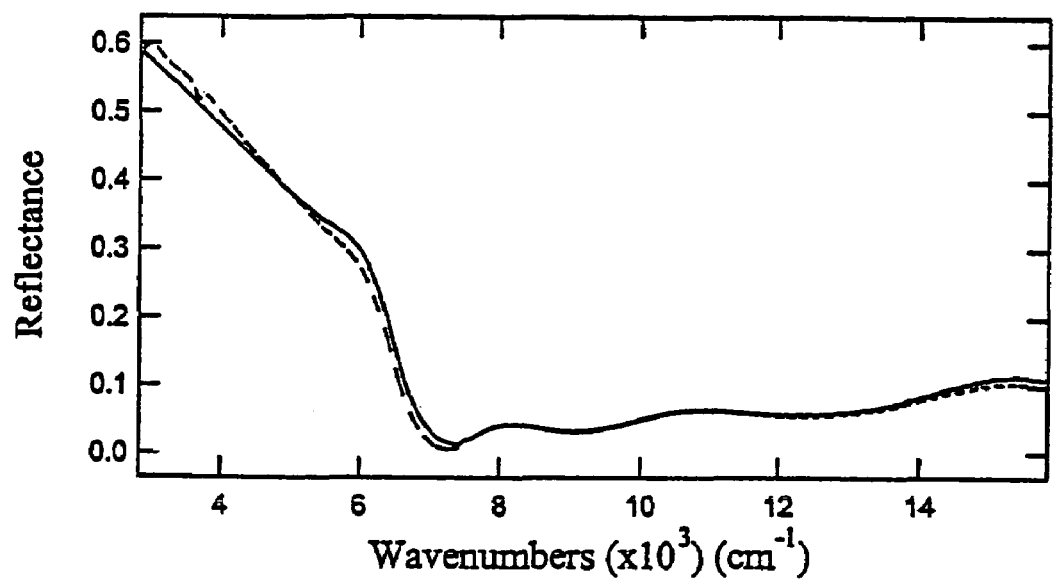
FIG. 9 is the reflectance FTIR spectra of ITO on a quartz substrate obtained with the IR radiation impinging either directly on the ITO thin film (solid line) or traveling through a quartz substrate and then interacting with the thin film of ITO (dashed line)

FIG. 9 shows the reflectance FTIR spectra of ITO on a quartz substrate obtained with the IR radiation impinging either directly on the ITO thin film (solid line) or first traveling through the quartz substrate and then interacting with the thin film of ITO (dashed line) using p-polarized IR radiation and an incident angle of 60 degrees. These spectra show the overall observed reflectance and plasmon frequency are nearly identical for these two sample geometries since quartz is optically transparent in this region (near-IR). The dielectric function of ITO could vary as molecules (such as DNA, proteins, antibodies) bind to the surface and could be monitored using the position of the plasmon frequency in a non-intrusive manner with the IR radiation impinging on the reverse (quartz) side of the ITO electrode.

Figure 10:
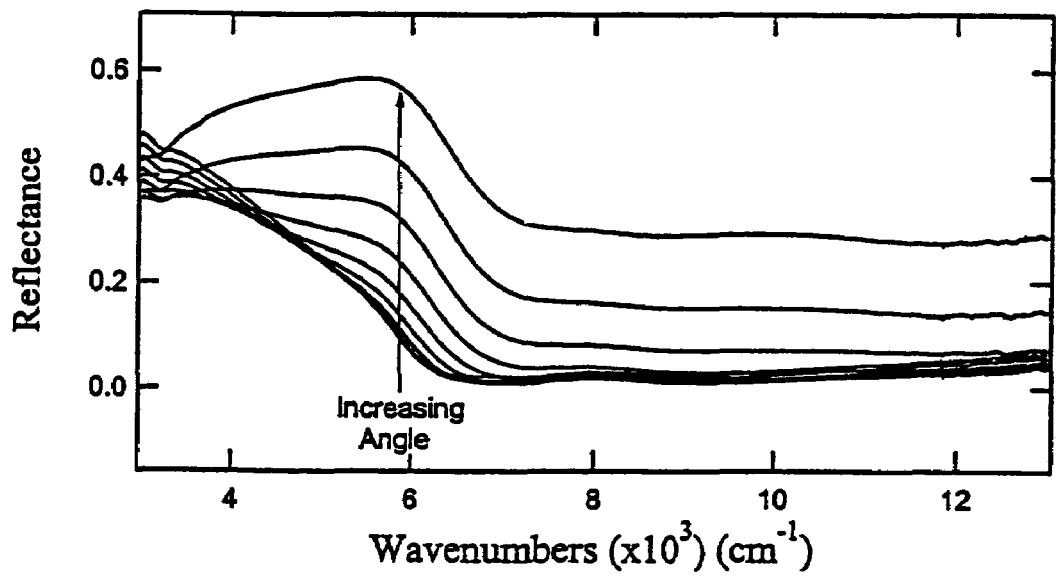
FIG. 10 is the reflectance FTIR spectra of a fluorine-doped tin oxide (SFO) film deposited on a glass substrate.

Other metal oxide thin films, such as fluorine-doped tin oxide (SFO) and iridium oxide, have similar optical properties as ITO in the near-IR. FIG. 10 shows the observed reflectance FTIR spectra of a SFO deposited on a glass substrate for incident angles of 40 to 80 degrees with a sheet resistance of 55.6 $\Omega/\square$ recorded with p-polarized radiation in the near-IR region with air/SFO sampling geometry. The overall reflectivity of this thin film and the observed plasmon frequency was lower than the ITO thin films studied. However the overall trends in the reflectance were similar to the observed ITO films shown in FIGS. 6–9. This decrease in reflectance may be due to the higher sheet resistance (55.6 $\Omega/\square$) of SFO than the ITO films studied. The change in the observed plasmon frequency may be due to differences in the charge carrier density and effective electron mass of SFO compared to ITO.

Figure 11:
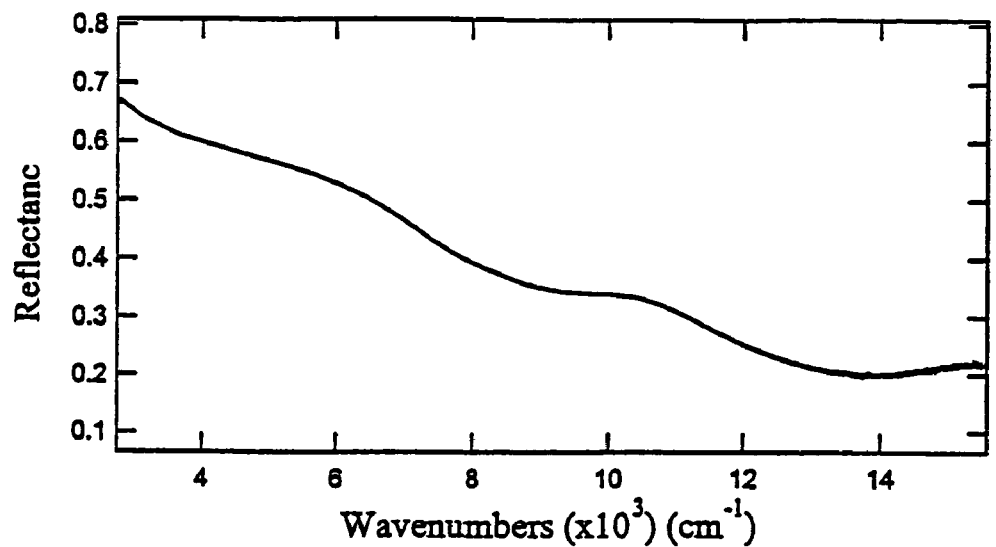
FIG. 11 is the reflectance FTIR spectra of a thin film of iridium oxide on a glass substrate.

The reflectance of a thin film of iridium oxide on a glass substrate is shown in FIG. 11. The reflectance spectra is of a 110 nm film of iridium oxide on a glass substrate recorded with an incident angle of 60 degrees and p-polarized radiation. The deposition conditions included a direct current magnetron reactive sputtering deposition using an Ir target, Ar:$O_2$ ratios of 7:3 gases, 30 mTorr total pressure with 150 W direct current power at a deposition rate of about 1 nm/s annealed in a standard furnace with fast fire techniques at 700° C. in air for ten minutes. The reflectance of this metal oxide also shows a downward trend throughout the near-IR spectral region.

As shown by FIGS. 6–11, the plasmon frequency of indium tin oxide (ITO) thin films was observed experimentally by variable angle reflectance FTIR spectroscopy and was found to decrease as the sheet resistance of the ITO thin films increased. The electronic scattering time and reflectance of these films also decreased with increasing sheet resistance. The Drude free-electron model and the two- or three-phase Fresnel equations of reflection can be used to fit the experimental data to obtain values for the plasmon frequency and electronic scattering time for the ITO thin films. These models may accurately describe the area near the plasmon frequency, however, the two-phase model overestimated the absolute reflectance of the ITO thin films at lower wavenumbers than the plasmon frequency. The three-phase Fresnel equations of reflection may accurately describe the experimental data more closely throughout the entire near-IR region investigated. The calculated values of the plasmon frequency or electronic scattering time differed by ~100–250 $cm^{-1}$ and 5–6 ($\times 10^{-16}$) s, respectively between the two- and three-phase Fresnel equations of reflection. As expected from the Fresnel equations of reflection, the observed plasmon frequency of ITO and reflectance just prior to the plasmon frequency decreased with decreasing angles of incidence for p-polarized radiation. Fluorine-doped tin oxide (SFO) thin films were found to be less reflective and had a lower observed plasmon frequency than the ITO thin films studied. Due to the optical properties of these metal oxide thin films, especially the plasmon frequency, these properties may be used to monitor surface events such as adlayer formation, binding of molecules to the surface, or chemical modification of these films. The two different sampling geometries offer flexibility in monitoring the observed surface plasmon frequency of these two metal oxide thin films during such surface modification/annealing procedures.

EXAMPLE 2

Correlation of Reflectivity and Skin Depth with Conductivity

Figure 12:
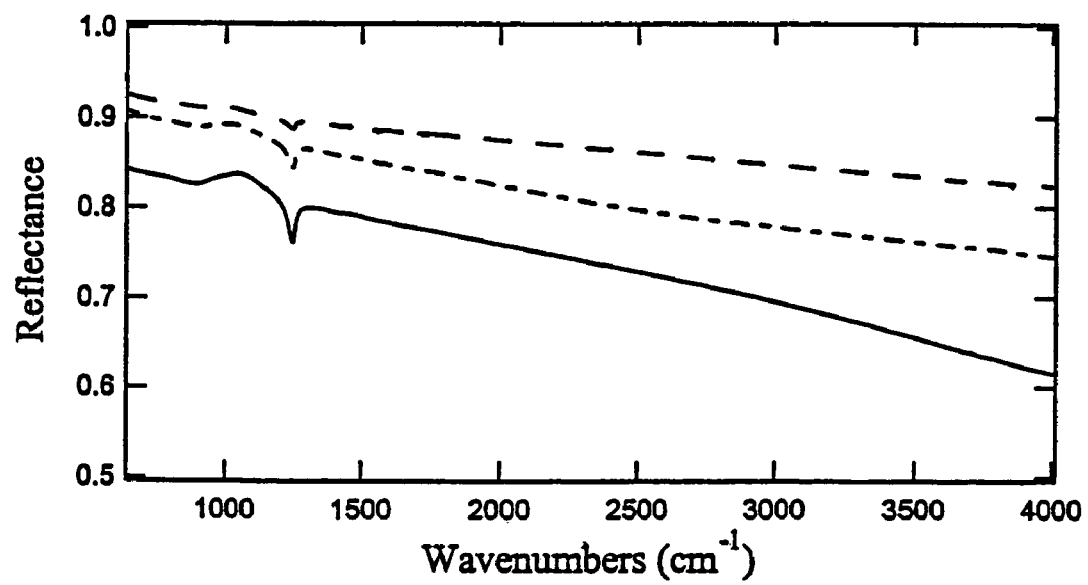
FIG. 12 is the reflectance FTIR spectra of ITO electrodes with various sheet resistance.

FIG. 12 shows the reflectance FTIR spectra of three ITO electrodes with various sheet resistances corresponding to an incident angle of 70 degrees and p-polarized IR radiation. The resistances shown are 12 (solid line), 9.0 (- -- -), and 6.8 (-- --) $\Omega/\square$. FIG. 12 shows that the reflectivity of ITO for this set of experimental parameters decreases as the sheet resistance is increased. The skin depth is affected as the resistances of the ITO substrates are varied. The skin depth ($\delta$) is related to the decay of the magnitude of the electric vector (E) in ITO by (Equation 15):

$$E = E_o \exp(-t/\delta) \tag{15}$$

where t is the thickness of ITO and $E_o$ is original magnitude of the electric vector. Equation 15 is discussed in Wooten, F. *Optical Properties of Solids;* Academic Press, Inc.: San Diego, 1972.

Figure 13:
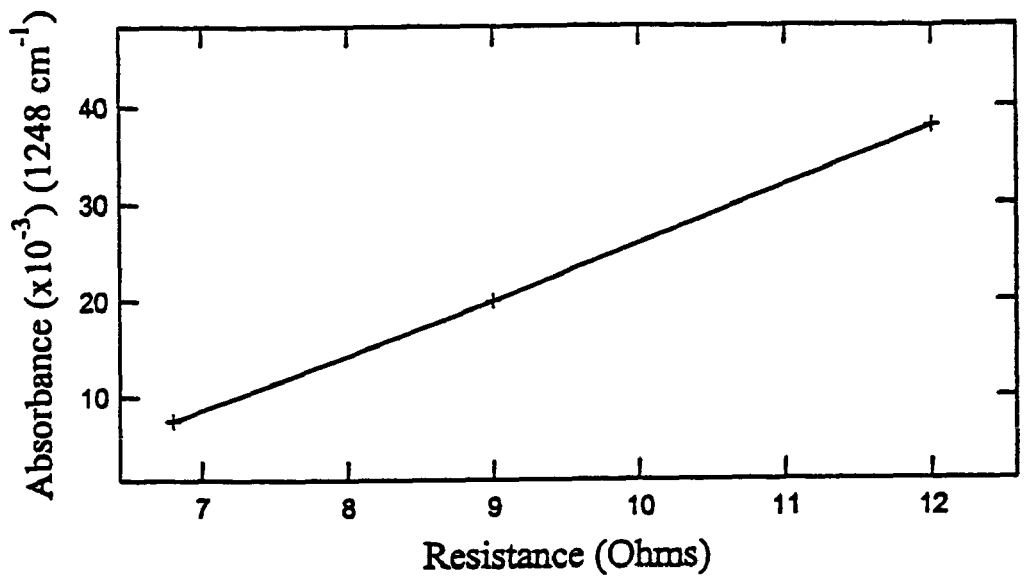
FIG. 13 is a graph of the absorbance of the glass substrate longitudinal optional (LO) mode at 1248 $cm^{-1}$ of silicon dioxide as a function of resistance.

The skin depth ($\delta$) can also be related to the conductivity as described in Equation 16, which is discussed below. FIG. 13 illustrates the relationship between conductivity and skin depth ($\delta$) by showing the resonant absorbance of the glass substrate longitudinal optional (LO) mode at 1248 $cm^{-1}$ of silicon dioxide) under the ITO thin film. The absorbance is determined by the skin depth of ITO.

Figure 14:
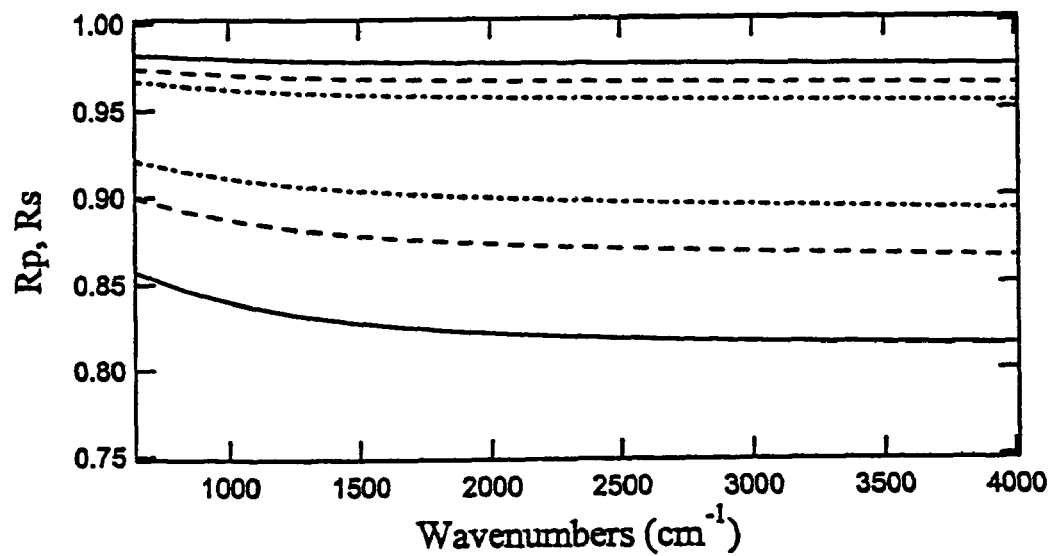
FIG. 14 is the calculated power reflectivity of ITO.

FIG. 14 shows the calculated power reflectivity of ITO using literature values for the Hall mobility (35 $cm^2V^{-1}s^{-1}$), free carrier concentration ($6\times 10^{20}$ $cm^{-3}$), and the bare electron mass. Fan, J.; Bachner, F.; Foley, G. *Applied Physics Letters* 1977, 31, 773–775. The calculation is based on the Fresnel equations of reflection. The top three curves are for s-polarized radiation and the bottom three curves are for p-polarized radiation. The incident angles of 70 (solid line), 60 (- - -), and 50 (- -- -) degrees are shown. FIG. 14 demonstrates that for s-polarized radiation in the mid-IR region, the power reflectivity decreases as the incident angle decreases. The reverse trend is seen for p-polarized radiation. Also, the power reflectivity for s-polarized radiation is greater for each incident angle shown than the corresponding incident angle for p-polarized radiation. These calculated results are in agreement with the observations made on ITO thin films above.

The measured sheet resistances of these ITO electrodes are directly related to the classical skin depth as define in the Drude free electron model for metals. The skin depth is defined by (Equation 16):

$$\delta = \frac{c}{(2\pi\sigma\mu\omega)^{1/2}} \tag{16}$$

where c is the speed of light and $\sigma$ is the conductivity. The conductivity is defined as (Equation 17):

$$\sigma = \frac{ne^2\tau}{m} \frac{1}{1 - i\omega\tau} \tag{17}$$

Equations 16 and 17 are discussed in Wooten, F. *Optical Properties of Solids;* Academic Press, Inc.: San Diego, 1972.

Substituting into the previous equation, the skin depth is shown in Equation 18:

$$\delta = \frac{c}{\sigma}\left(\frac{ne}{2\pi\omega}\right)^{\frac{1}{2}} \tag{18}$$

Equation 18 may be accurate provided that $\omega\tau<<1$ and the skin depth ($\delta$) includes only of the real part of the conductivity σ. The resistance, R and the direct current resistivity, $\rho_{dc}$ are related to one another as shown in Equation 19:

$$\rho_{dc} = Rt = \frac{1}{\varepsilon_0 \omega_p^2 \tau} \quad (19)$$

where t is the thickness. Equation 19 is discussed in Stjerna, B.; Olsson, E.; Granqvist, C. *Journal of Applied Physics* 1994, 76, 3797–3817. Hence, the plasmon band is related to the resistance as shown in Equation 20:

$$\omega_p = \left(\frac{1}{Rt\varepsilon_0 \tau}\right)^{\frac{1}{2}} \quad (20)$$

Figure 15:
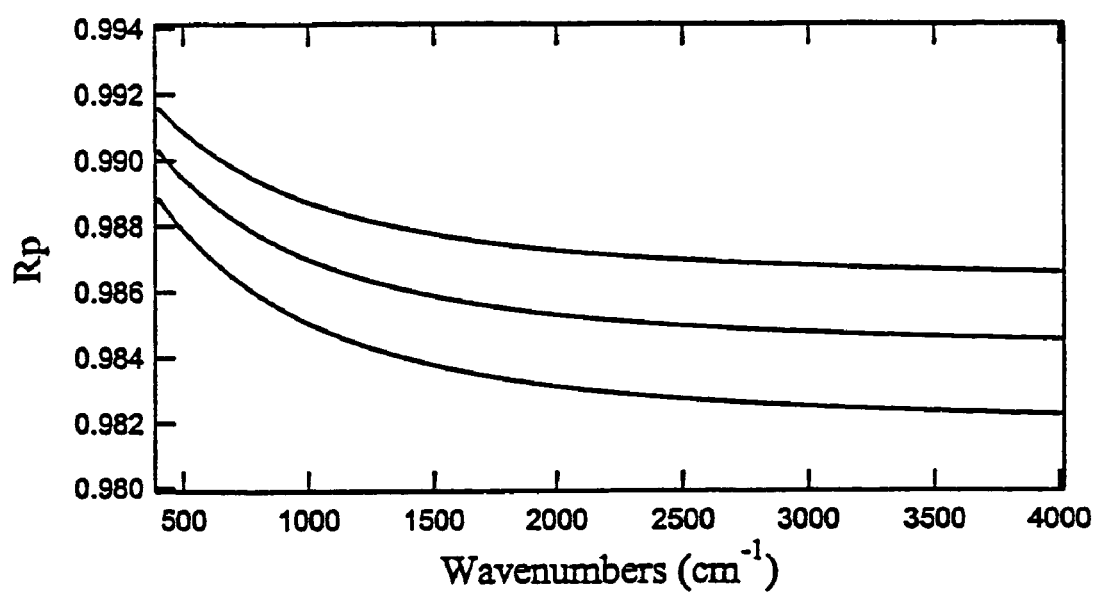
FIG. 15 is the calculated reflectance for various resistances at an incident angle of 70 degrees.

This relation is shown in FIG. 10 where the resistance is used to calculate the plasmon frequency (at a constant value for the electronic scattering time), which was used in the Drude model to calculate the optical properties needed for the Fresnel equations of reflection. FIG. 15 illustrates the calculated reflectance using Equations 6–10 for each of the resistances at an incident angle of 70 degrees and p-polarized radiation with a thickness of 1500 Å and a scattering time of $2\times10^{-14}$ s. The top line has a resistance of 6.8 Ω/□, the middle line has a resistance of 9.0 Ω/□ And the bottom line has a resistance of 12 Ω/□. FIG. 15 also demonstrates that as the ITO resistance increases, the calculated reflectance is in agreement with experimental observations.

Figure 16A:
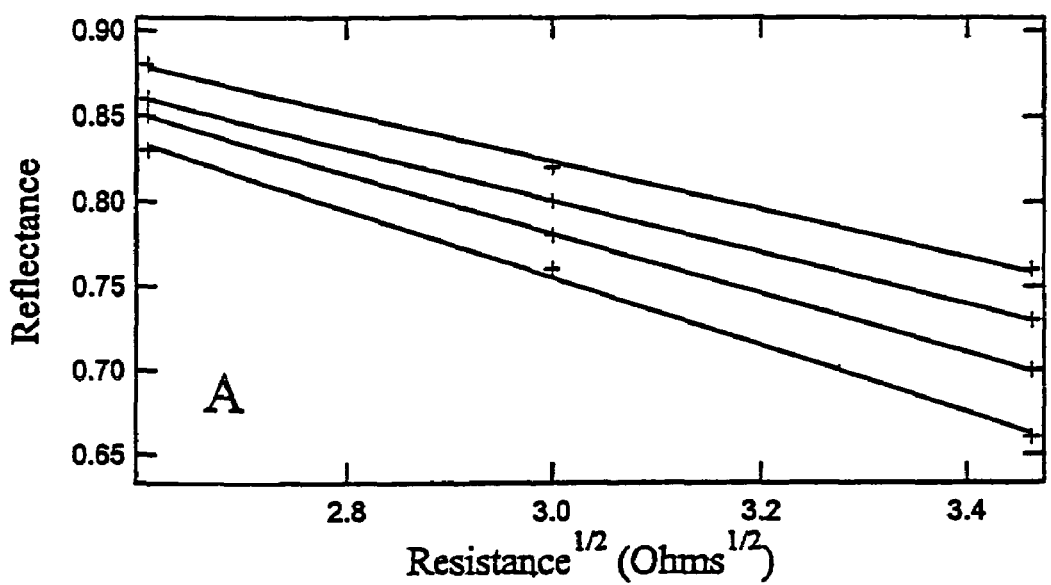
FIGS. 16A and 16B are the reflectance and the calculated power reflectivity, respectively, for p-polarized radiation on ITO film.
Figure 16B:
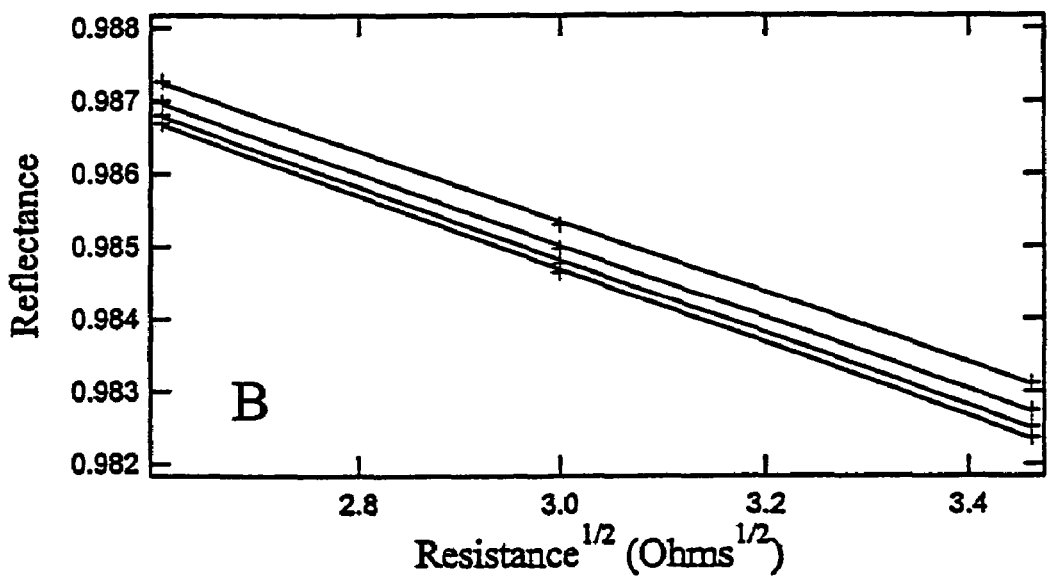

FIGS. 16A and 16B illustrate the observed reflectance and the calculated power reflectivity, respectively, for an incident angle of 70 degrees and p-polarized radiation on an ITO film. The plots shown refer from top to bottom to incident light wave numbers of 2000, 2500, 3000, and 3500 cm$^{-1}$, respectively. FIGS. 16A and 16B illustrate that the experimentally observed reflectance and the calculated power reflectivity of ITO vary linearly with the square root of the resistance for p-polarized radiation and an incident angle of 70 degrees. Therefore, the sheet resistance and the skin depth are related as shown by Equation 21:

$$\delta = Rtc\left(\frac{ne}{2\pi\omega}\right)^{\frac{1}{2}} \quad (21)$$

The experimental measurement in FIG. 13 would suggest that the skin depth is directly proportional to resistance in the ITO samples with slightly different preparation. However, when ITO is compared to SFO, both n and τ differ such that SFO does not follow the linear correlation shown in FIG. 13 and Equation 21. SFO has a higher sheet resistance (about 55 Ω/□) and corresponding greater skin depth and lower reflectivity as expected based on the above equations. Quantitative comparison of these equations for two different materials such as ITO and SFO would require independent measurement of the plasmon frequency. Such measurements are possible in a grazing angle configuration and the plasmon frequencies are expected to occur in the range 5,000–10,000 cm$^{-1}$ for ITO based on both calculated values of n and τ and experimental data. The plasmon frequency for SFO is expected to be lower than that for ITO.

As shown in FIGS. 12–16, the reflectance of ITO and SFO may be observed to be a function of incident angle, wavenumber, and polarization for a given electrode. The reflectance of ITO appeared higher than SFO in the mid-IR region. Additionally, the skin depth was shown theoretically and experimentally to vary linearly with the sheet resistance of ITO. The experimental reflectance and calculated power reflectivity of ITO varied linearly with the square root of the sheet resistance. Grazing angle FTIR spectroscopy may be used to probe the conducting properties based on the correlation with the reflectance and skin depth of ITO thin films. Such properties may be generally observed for thin films of metal oxides and mixed metal oxides when absorptive infrared bands are present in the substrate.

EXAMPLE 3

Detection of Surface Adlayers

The stability of self-assembled monolayers is determined both by the bonding interaction with the metal or metal chalcogenide substrate and the hydrophobic effect between aliphatic regions of adlayer molecules. The determination of the relative strength of these competing factors on gold has been well studied, particularly in the case of the family of derivatized alkane thiols. Ulman, A. *Chemical Reviews* 1996, 96, 1533–1554. Lavrich, D.; Wetterer, S.; Bernasek, S.; Scoles, G. *Journal of Physical Chemistry B*, 1998, 102, 3456–3465.

Because thiols have been widely used for the creation of self-assembled monolayers, it is logical to consider their application on metal oxides. However, the interaction of thiols with metal oxides is not necessarily as strong as that with gold. Thiols (or thiolates) were compared with phosphonates and sulfonates on indium tin oxide (ITO) and fluorine doped tin oxide (SFO) surfaces. While thiols and phosphonates form stable surface layers for alkane chain lengths of greater than 16 and 12 respectively, sulfonates do not form stable adlayers. The formation of adlayers is documented by variable angle reflectance Fourier transfer infrared (FTIR) spectroscopy and X-ray photoelectron spectroscopy (XPS).

1-Hexadecanethiol, dodecanethiol, octanethiol, and dimethyl sulfoxide (DMSO) were used as received from Sigma-Aldrich, St. Louis, Mo., U.S.A. Sodium Dodecyl Sulfate (SDS) was used as received from Bio-Rad Laboratories, Hercules, Calif., U.S.A. 12-Phosphonododecanoic acid was obtained from Xanthon, Inc., Research Triangle Park, N.C., U.S.A. Millipore 18 MΩ deionized water (BARNSTEAD E-PURE™ from Barnstead International, Dubuque, Iowa., U.S.A.) was used for aqueous solutions. Indium Tin Oxide (ITO) electrodes were received from Delta Technologies, Limited, Stillwater, Minn., U.S.A. and were had a composition containing 90% indium oxide and 10% tin oxide. The ITO electrodes had a nominal thickness of 1,500 Å and a sheet resistance of 8–12 Ω/□. The substrate for the ITO electrodes was polished float (soda-lime) glass. The fluorine doped tin oxide (SFO) electrodes were obtained from PPG Industries, Inc., Pittsburgh, Pa., U.S.A., and had a sheet resistance of 49–51 Ω/□. The gold electrodes were obtained from Evaporated Films, Inc.

Deposition on ITO and SFO Electrodes.

The ITO and SFO electrodes were cleaned via 20 minutes of UV/O$_3$ (UVO-cleaner (UVO-60), model number 42, Jelight Company, Inc., Irvine Calif., U.S.A.) to yield a clean hydrophilic surface as determined by water contact angle measurements made using a NRL C.A. Goniometer from Rame-Hart, Inc., Mountain Lakes, N.J., U.S.A., model 100–00. The sheet resistances of these electrodes were measured with a 4-point probe consisting of a SIGNA-TONE™ D27M probe station from Signatone Corporation, Gilroy, Calif., U.S.A.; a KEITHLEY™ 224 programmable current source from Keithley Instruments, Cleveland, Ohio, U.S.A; and a 3456A digital voltmeter from Hewlett Packard, Palo Alto, Calif., U.S.A. The clean electrodes were dried by $N_2$ gas and were then immersed for 16 hours in one of the deposition solutions. The deposition solutions were 10 mM 12-phosphonododecanoic acid in DMSO or 50/50 (v/v) DMSO/18 MΩ·cm $H_2O$, 10 mM SDS in 18 MΩ·cm $H_2O$ or 50/50 (v/v) DMSO/18 MΩ·cm $H_2O$, neat 1-hexadecanethiol, neat dodecanethiol, and neat ocatanethiol. Then electrodes immersed in either 12-phosphonododecanoic acid or SDS were rinsed with 18 MΩ·cm $H_2O$ followed by drying the electrodes with $N_2$ gas. The electrodes immersed in 1-hexadecanethiol, dodecanethiol, or octanethiol were rinsed with ethanol and dried with $N_2$ gas. Then the electrodes first immersed in neat 1-hexadecanethiol (16 hours) were then immersed in 10 mM 12-phosphonododecanoic acid in 50/50 (v/v) DMSO/18 MΩ·cm $H_2O$ (16 hours), rinsed with 18 MΩ·cm $H_2O$, and dried with $N_2$ gas. Also the electrodes first immersed in 10 mM 12-phosphonododecanoic acid in 50/50 (v/v) DMSO/18 MΩ·cm $H_2O$ (16 hours) were then immersed in 1-hexadecanethiol (16 hours), rinsed with ethanol, and dried with $N_2$ gas.

Reflectance FTIR Spectroscopy. The variable angle reflectance FTIR spectra were recorded using a SPECTRA-TECH™ VEEMAX™ variable angle reflectance attachment available from Spectra-tech, Madison, Wis., U.S.A. in a NICOLET™ 550 Magna-IR spectrometer available from Thermo-Nicolet, Lanham, Mass., U.S.A. The angle of incidence ranged from 40–70 degrees. An infrared polarizer was used to obtain s-(horizontal) or p-(vertically) polarized light. A ratio of the single beam spectra of bare ITO electrodes, SFO electrodes, or glass to a single beam spectrum of a gold electrode was performed to obtain the reflection spectrum of the ITO, SFO, or glass. The spectra of the material deposited on the electrodes were obtained by taking a ratio of the single beam spectra of the deposited material on the electrode to one of the bare electrode. The rotational lines from gaseous water were subtracted from these spectra. The solid and solution FTIR spectra of the compounds were taken using an IR microscope (model number UMA-500) attached to a BIO-RAD™ DIGILAB™ FTS 6000 FTIR spectrometer (Bio-Rad Laboratories, Hercules, Calif., U.S.A.) equipped with a Cassegranian objective containing a germanium crystal for single pass attenuated total reflection (ATR). Both FTIR spectrometers were equipped with a liquid nitrogen cooled Metal-Oxide-Semiconductor Controlled Transistor (MCT) detector and were recorded at a resolution of 4 $cm^{-1}$ with a spectral range of 650–4000 $cm^{-1}$. All IR spectra were the result of the average of 256 scans and were recorded at room temperature.

X-ray Photoelectron Spectroscopy (XPS). XPS spectra were recorded on a RIBER™ LAS 2000 Surface Analysis System (Riber, Paris, France) equipped with a cylindrical mirror analyzer (CMA) and an electron analyzer such as a MAC2 analyzer with Mg Kα x-rays (model CX 700 (RIBER™ source) (hv=1253.6 eV). The elemental scans had a resolution of and were the result of either 5 or 20 scans (all spectra were normalized to 5 scans). XPS spectra were smoothed using a 9 point (second order) Savitzky-Golay algorithm, baseline corrected, and the peaks were fitted using Gaussian/Lorenztian (90/10) line shapes. The phosphorus and sulfur 2p 3/2 and 1/2 angular momentum components were fit with a fixed 2:1 peak area ratio.

Results

Figure 17A:
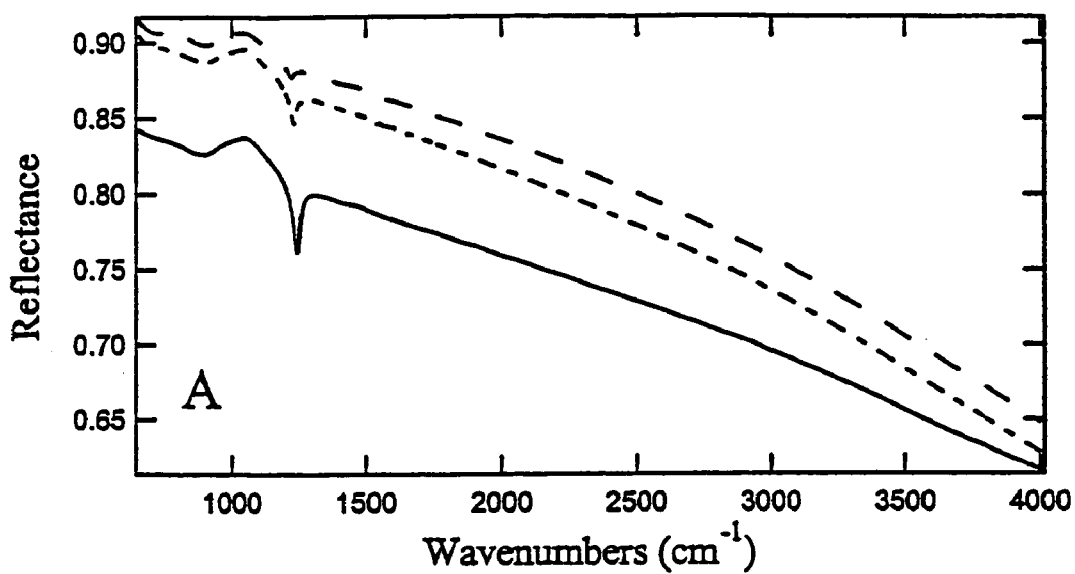
FIGS. 17A and 17B are the variable angle reflectance FTIR specra of ITO electrodes.
Figure 17B:
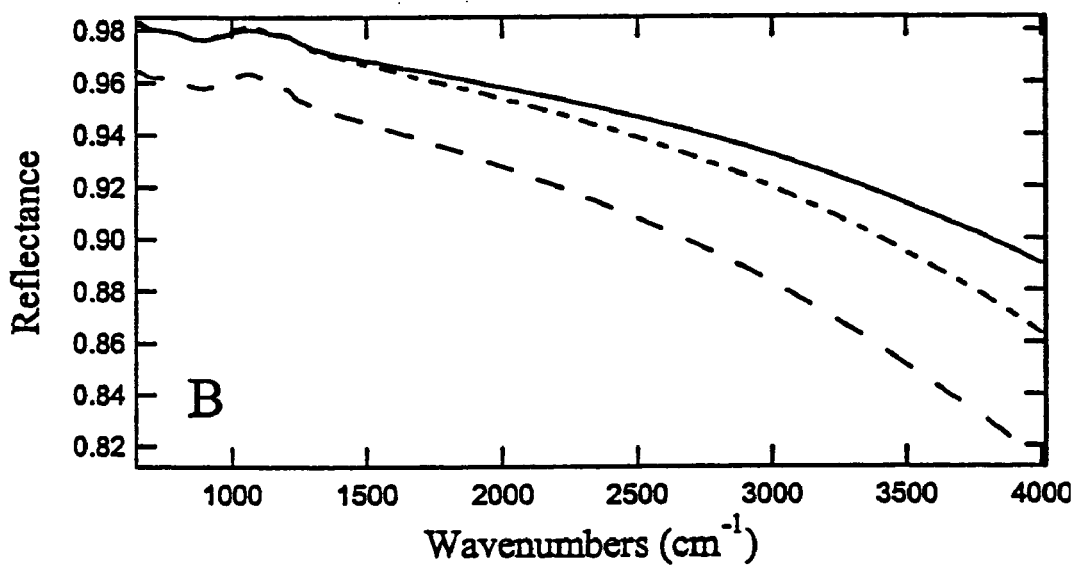

Reflectance FTIR Spectra of ITO. ITO films have sufficiently high reflectivity in the infrared region to permit determination of reflectance FTIR spectra on ITO in a grazing angle geometry. FIGS. 17A and 17B show the variable angle reflectance FTIR spectra of an ITO electrode for angles of incidence of 50° (-- --), 60° (- - -) and 70° (solid line) for p- and s-polarized light, respectively. The spectra are obtained from a ratio of ITO electrode spectra to gold spectra. Features of these spectra may be considered in optical detection of adlayer formation, for example, the relatively high reflectance of ITO in the mid-IR. For p-polarized light usually employed in studies on metallic surfaces (due to surface selection rules) in the grazing angle geometry, the reflectance is generally greater than 0.7 in the methylene ($CH_2$) stretching region near 3000 $cm^{-1}$. The reflectance for both p- and s-polarized spectra decreases in the wavenumber range from 1500 to 4000 $cm^{-1}$ due to the onset of the plasmon absorption of ITO as discussed herein. The reflectance for the p-polarized spectra increases with decreasing angle of incidence, while the opposite is true for s-polarized light. The relationship of reflectance to angle of incidence suggests that an angle of 50–70 degrees may be optimal for detection of surface adlayers. The longitudinal optical (LO) Si—O—Si stretching mode is observed at 1248 $cm^{-1}$ for 70 degrees of incidence and decreases to 1236 and 1229 $cm^{-1}$ for 60 and 50 degrees, respectively. The Si—O—Si stretching mode is a characteristic of the glass. The correlation of the intensity of this band to the skin depth of the ITO film is discussed herein. In this example, interference from the glass bands can complicate the analysis of any features from surface adlayers that may fall in the region from 900–1300 $cm^{-1}$. However, certain features may occur elsewhere in the spectrum and may be distinguished from the glass bands.

Deposition of Alkane Thiols, Phosphonates, and Sulfonates.

Figure 18A:
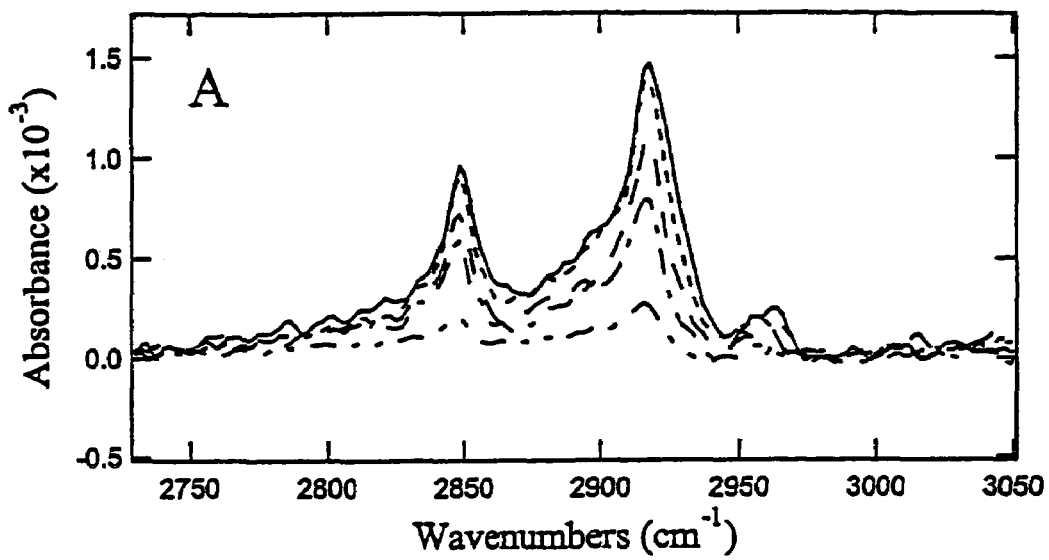
FIG. 18A is the variable angle reflectance spectra of a 1-hexadecanethiol adlayer on an ITO electrode.
Figure 18B:
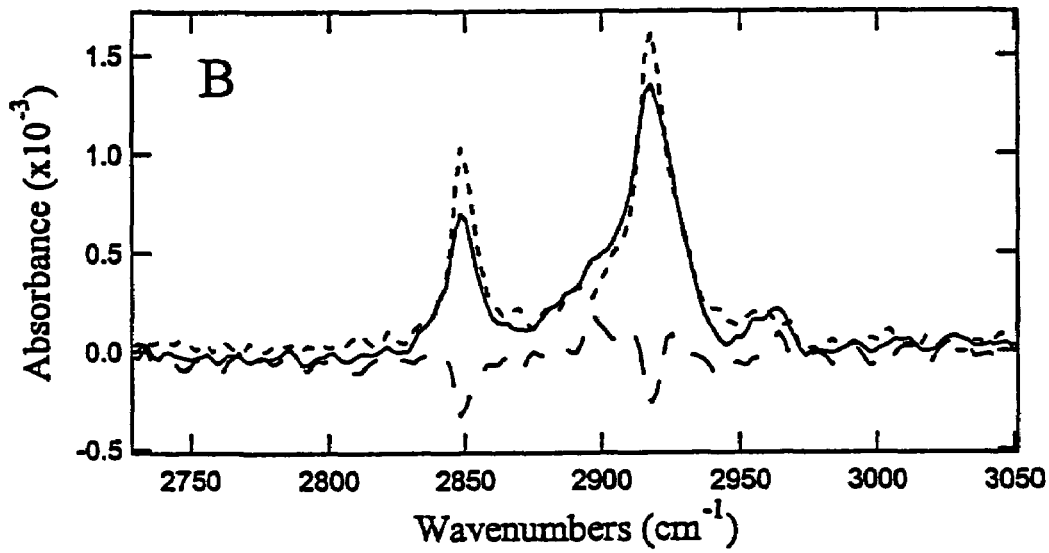
FIG. 18B is the subtraction of the spectrum of 1-hexadecanethiol on ITO from the spectrum of 1-hexadecanethiol on SFO.

FTIR Characterization. FIG. 18A shows the variable angle reflectance FTIR spectra of a 1-hexadecanethiol adlayer on an ITO electrode. Spectra shown are for angles of incidence of 40 (- - - --), 50 (-- ---), 60(- - -) and 70 (solid line) degrees for p-polarized IR light and 70 degrees for s-polarized light (-- - - --). The first peak at 2848 $cm^{-1}$ corresponds to the a normal mode frequency of the symmetric $CH_2$ stretches, the second peak at 2918 $cm^{-1}$ corresponds to the normal mode frequency of the asymmetric $CH_2$ stretches, and the third peak at 2961 $cm^{-1}$ for ITO and 2959 $cm^{-1}$ for SFO correspond to the normal mode frequency of the asymmetric $CH_3$ stretches. The intensity of the peaks corresponding to the symmetric and asymmetric vibrational modes of the $CH_2$ groups and asymmetric $CH_3$ stretches decrease as the incident angle for the p-polarized spectra decreases. The observed peaks for the s-polarized spectrum at 70° of incidence are significantly less intense as compared to the p-polarized spectra at the same angle of incidence. FIG. 18B shows a baseline corrected reflectance FTIR spectra having an incidence angle of 70 degrees with p polarized radiation obtained from a ratio of 1-hexadecanethiol on ITO to bare ITO (solid line), a ratio of 1-hexadecanethiol on SFO to bare SFO (- - -), and the subtraction of the spectrum of 1-hexadecanethiol on ITO from the spectrum of 1-hexadecanethiol on SFO (-- -- --). The bare (reference) substrate was cleaned via 20 minutes of UV/O3. The monolayer deposition occurred for 16 hour.

As shown by FIG. 18B, the subtraction of the spectrum of 1-hexadecanethiol on ITO from the spectrum of 1-hexadecanethiol on SFO (-- -- --) illustrates that the peak widths of the $CH_2$ and $CH_3$ vibrational stretches are the same for the monolayer on both electrodes. However, the intensity of the signal is greater on SFO. Normal mode frequencies of neat 1-hexadecanethiol and frequencies corresponding to a monolayer of 1-hexadecanethiol on ITO and SFO respectively at an incidence angle of 70 degrees with p-polarized light are shown in Table 3.

TABLE 3

|  | Neat (liquid) | ITO | SFO |
|---|---|---|---|
| $v_sCH_2$ (cm$^{-1}$) | 2851 | 2848 | 2848 |
| $v_aCH_2$ (cm$^{-1}$) | 2920 | 2918 | 2918 |
| $v_aCH_3$ (cm$^{-1}$) | 2953 | 2961 | 2959 |

Figure 19A:
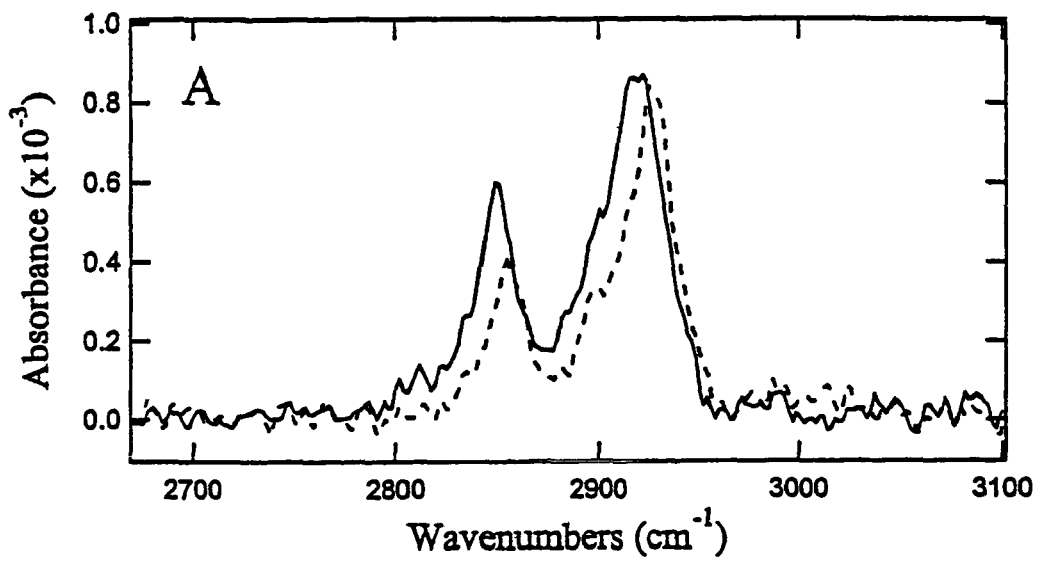
FIGS. 19A and 19B are baseline corrected reflectance FTIR spectra obtained from a ratio of 12-phosphonododecanoic acid and dimethyl sulfoxide (DMSO) on ITO and bare ITO.
Figure 19B:
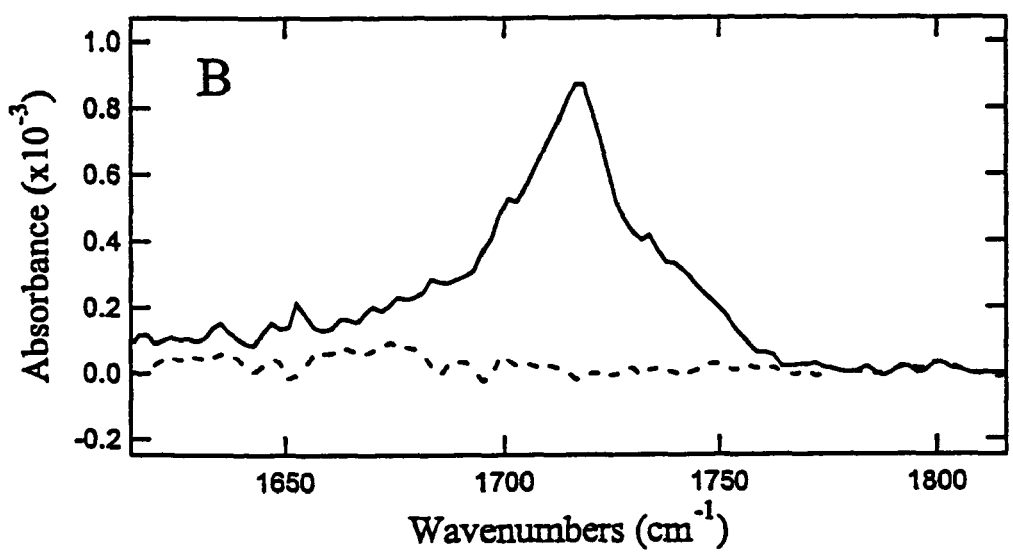

FIGS. 19A and 19B are baseline corrected reflectance FTIR spectra obtained from a ratio of 12-phosphonododecanoic acid (deposited from 50/50 (v/v) DMSO/18 MΩ·cm $H_2O$ (solid line), and DMSO (dashed line) on ITO to bare ITO. Spectra shown are for an incident angle of 70 degrees and p-polarized IR light. The spectra were obtained from a ratio of 12-phosphonododecanoic acid on ITO to bare ITO. The bare (reference) ITO substrate was cleaned via 20 minutes of UV/$O_3$, and the monolayer deposition on the 12-phosphonododecanoic acid substrate occurred for 16 hours. The spectra in FIG. 19A show vibrational modes corresponding to the symmetric and asymmetric stretching motions of $CH_2$ groups. The peak at about 2850 cm$^{-1}$ corresponds to the symmetrical stretching vibration of $CH_2$, and the peak at about 2925 cm$^{-1}$ corresponds to the assymetrical stretching vibration of $CH_2$. As seen in FIG. 19B, the carbonyl stretching vibration is observed only for the adlayer formed from 50/50 (v/v) DMSO/18 MΩ·cm $H_2O$ deposition solution. The values of the vibrational frequencies of the adlayer or partial adlayer structures of 12-phosphonododecanoic acid on ITO, SFO and the corresponding solid and solution values of these modes at an incident angle of 70 degrees is shown in Table 4.

TABLE 4

|  | Solid | solution | ITO[a] | ITO[b] | SFO[a] | SFO[b] |
|---|---|---|---|---|---|---|
| $v_sC=O$ (cm$^{-1}$) | 1686 | 1721 | 1716 | — | — | — |
| $v_sCH_2$ (cm$^{-1}$) | 2845 | 2851 | 2848 | 2854 | 2850 | 2862 |
| $v_aCH_2$ (cm$^{-1}$) | 2914 | 2928 | 2922 | 2926 | 2924 | 2926 |

([a]50/50 (v/v) DMSO/18 MΩ · cm $H_2O$,
[b]DMSO deposition solution)

The variable angle reflectance FTIR spectra of a partial adlayer of 12-phosphonododecanoic acid on a SFO electrode deposited from either DMSO (a) or 50/50 (v/v) DMSO/18 MΩ·cm $H_2O$ (b) show low intensity modes (below approximately 400×10$^{-6}$ absorbance units) for 70 degrees incident angle and p-polarized infrared light (data not shown) in the methylene ($CH_2$) symmetric and asymmetric stretching region. These modes have a lower intensity and different peak profile as compared to the corresponding modes of an adlayer of 12-phosphonododecanoic acid on ITO. The values of the various vibrational frequencies of the partial adlayer structures of 12-phosphonododecanoic acid on SFO are listed in Table 4.

The variable angle reflectance FTIR spectra of an ITO surface following application of sodium dodecyl sulfate (SDS) from 50/50 (v/v) DMSO/18 MΩ·cm $H_2O$ show low intensity peaks (below 3×10$^{-4}$ absorbance units) at 2848 and 2918 cm$^{-1}$, which correspond symmetric and asymmetric $CH_2$ stretching modes observed at 2849 and 2916 cm$^{-1}$, respectively in solid SDS. No observable modes in this region were observed from the deposition of SDS on ITO from 18 MΩ·cm $H_2O$ leading to the conclusion that no adlayer is formed under these conditions (see supplementary material). The variable angle FTIR spectra for SDS deposited on SFO electrodes from either 18 MΩ·cm $H_2O$ or 50/50 (v/v) DMSO/18 MΩ·cm $H_2O$ also do not show any detectable peaks corresponding to SDS on the surface further substantiating the conclusion that no adlayer is formed by SDS (data not shown).

Figure 20A:
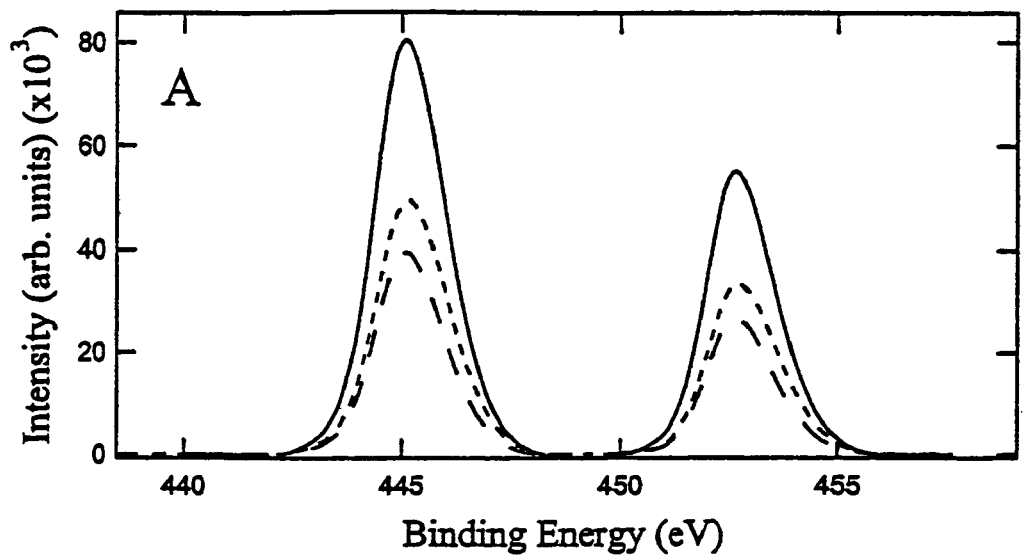
FIGS. 20A and 20B are XPS spectra of indium $3d_{5/2,3/2}$ (FIG. 20A) and tin $3d_{5/2,3/2}$ (FIG. 20B) of bare ITO (solid line) and an adlayer of either 1-hexadecanethiol or 12-phosphonododecanoic acid.
Figure 20B:
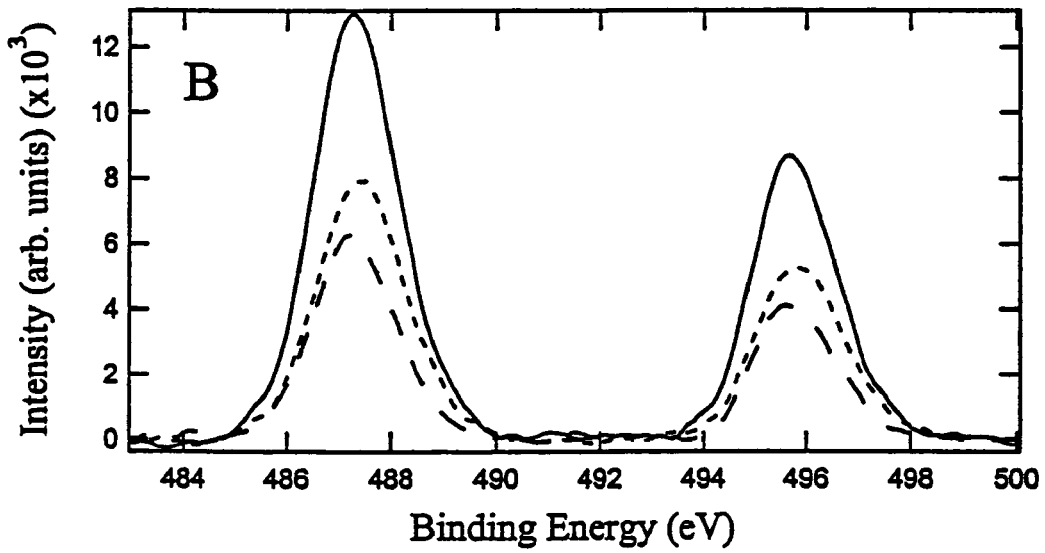
Figure 20C:
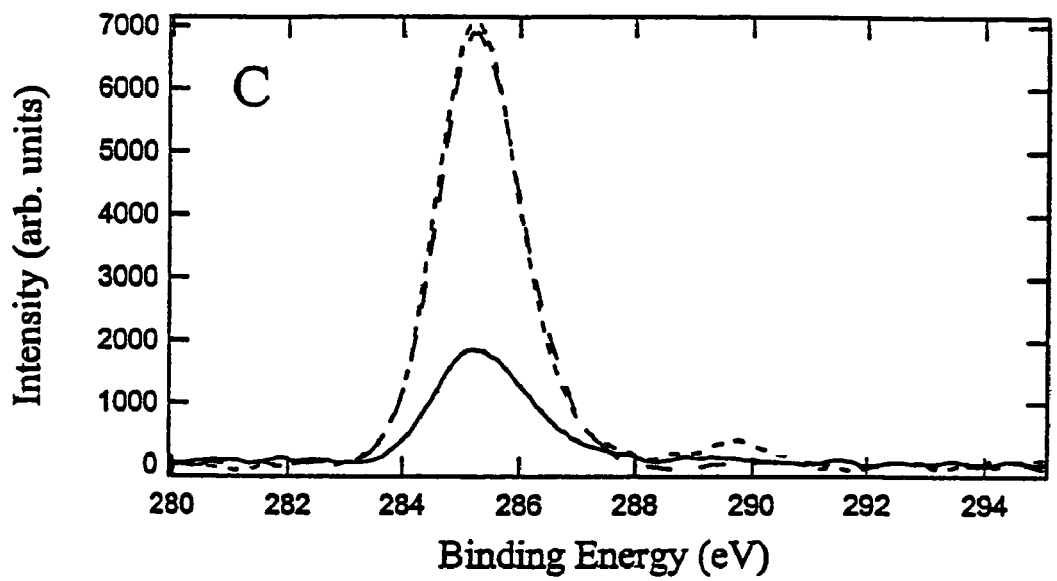
FIG. 20C is a carbon 1s spectra of bare ITO, 1-hexadecanethiol on ITO, and 12-phosphondododecanoic acid on ITO.

XPS Characterization. FIGS. 20A and 20B shows the XPS spectra of indium $3d_{5/2,3/2}$ (FIG. 20A) and tin $3d_{5/2,3/2}$ (FIG. 20B) of bare ITO (solid line) and an adlayer of either 1-hexadecanethiol (-- -- line) or 12-phosphonododecanoic acid (- - line) (deposited from 50/50 (v/v) DMSO/18 MΩ·cm $H_2O$) on ITO. The position of the indium $3d_{5/2,3/2}$ (445.1, 452.7 eV) and tin $3d_{5/2,3/2}$ (487.2, 495.7 eV) of bare ITO corresponds to the $In^{3+}$ and $Sn^{4+}$ oxidation states in ITO, respectively. Yan, C.; Zharnikov, M.; Golzhauser, A.; Grunze, M. *Langmuir* 2000, 16, 6208–6215. The spectra shown in FIGS. 20A and 20B illustrate a significant attenuation of these signals in the spectra corresponding to either a monolayer of 1-hexadecanethiol or 12-phosphonododecanoic acid on ITO relative to bare ITO. FIG. 20C is the carbon 1s spectra of bare ITO (solid line), 1-hexadecanethiol on ITO (-- -- line), and 12-phosphonododecanoic acid (- - line) on ITO. The carbon Is signal occurs at 285.2 eV (for adventitious carbon on bare ITO) and an increase in this peak is observed for either 1-hexadecanethiol or 12-phosphonododecanoic acid on ITO. An additional peak at 289.7 eV, corresponding to the carbon 1s peak of a carbon of a carbonyl group, is observed for 12-phosphonododecanoic acid on ITO. Yan C.; Zharnikov, M.; Golzhauser, A.; Grunze, M. *Langmuir* 2000, 16 6208–6215. Table 5 shows the results and a summary of the peaks for dodecanethiol, octanethiol, and sodium dodecyl sulfate.

TABLE 5

In $3d_{5/2, 3/2}$ (445.1, 452.7 eV), Sn $3d_{5/2, 3/2}$ (487.2, 495.7 eV), and C 1s (285.2 eV) XPS intensities and percentage differences from bare ITO reference.

|  | In $3d_{3/2}$ | In $3d_{5/2}$ | Sn $3d_{3/2}$ | Sn $3d_{5/2}$ | C 1s |
|---|---|---|---|---|---|
| Bare ITO | 55300 | 80664 | 8709 | 12994 | 1860 |
| 1-Hexadecanethiol | 26737 | 39577 | 4133 | 6287 | 6895 |
|  | (−52%) | (−51%) | (−53%) | (−52%) | (+271%) |
| Dodecanethiol | 40729 | 58617 | 6393 | 9118 | 3966 |
|  | (−26%) | (−27%) | (−27%) | (−30%) | (+113%) |
| Octanethiol | 44859 | 64854 | 7535 | 10736 | 2532 |
|  | (−19%) | −(20%) | (−13%) | (−17%) | (+36%) |
| 12-Phosphonododecanoic acid[a] | 33417 | 49442 | 5297 | 7930 | 7068 |
|  | (−40%) | (−39%) | (−39%) | (−39%) | (+280%) |
| 12-Phosphonododecanoic acid[b] | 44573 | 65276 | 6478 | 9969 | 4537 |
|  | (−19%) | (−19%) | (−26%) | (−23%) | (+144%) |
| Sodium Dodecyl Sulfate[c] | 49141 | 72095 | 7514 | 11554 | 2572 |
|  | (−11%) | (−11%) | (−14%) | (−11%) | (+38%) |

([a]50/50 (v/v) DMSO/18 MΩ · cm $H_2O$,
[b] DMSO,
[c]18 MΩ · cm $H_2O$ deposition solvent system)

Figure 21A:
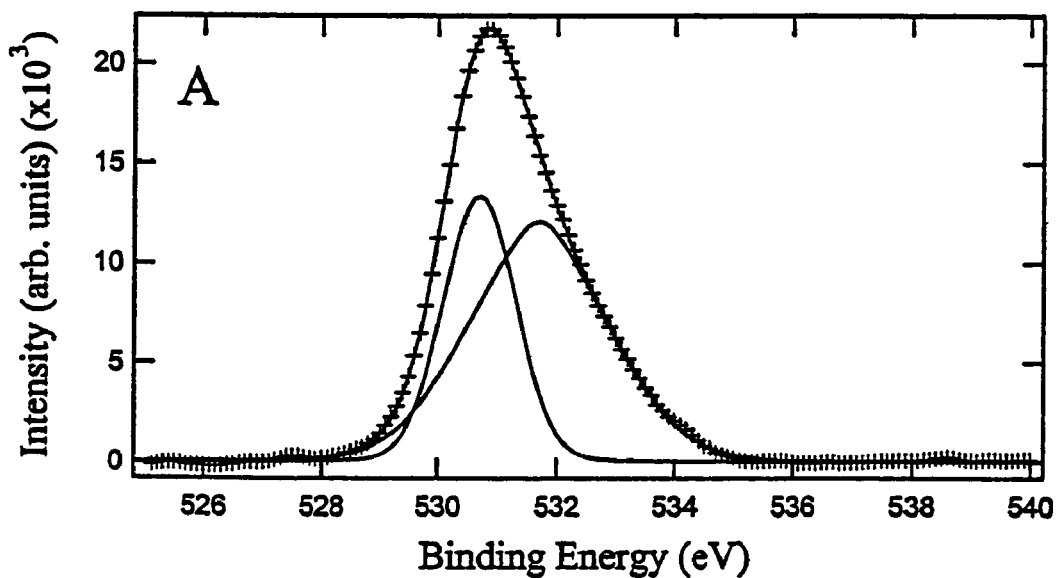
FIGS. 21A, 21B and 21C are XPS spectra of O 1s of bare ITO (FIG. 21A), an adlayer of 12-phosphonododecanoic acid on ITO (FIG. 21B), and an adlayer of 1-hexadecanethiol on ITO (FIG. 21C)
Figure 21B:
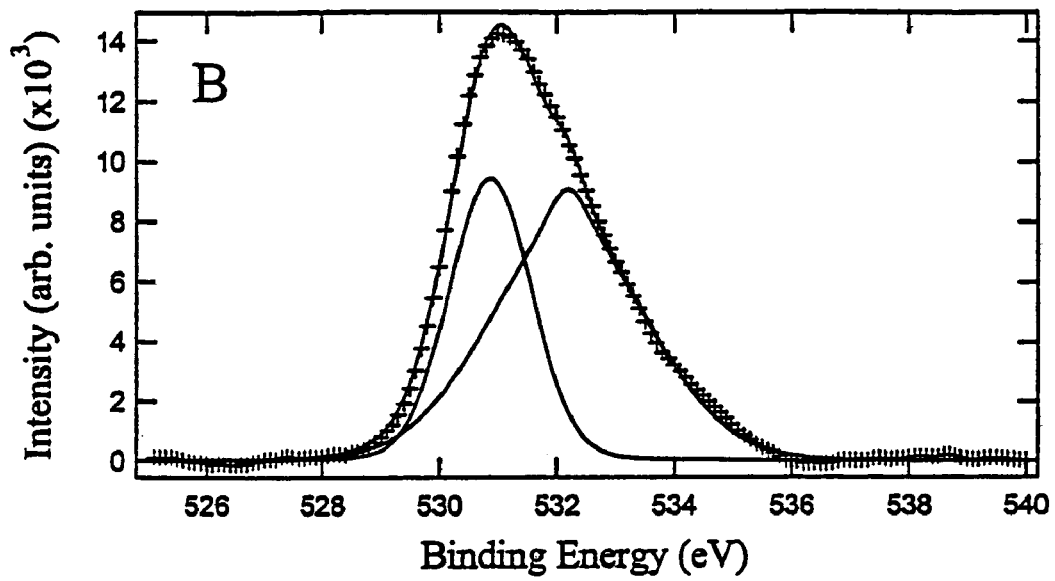
Figure 21C:
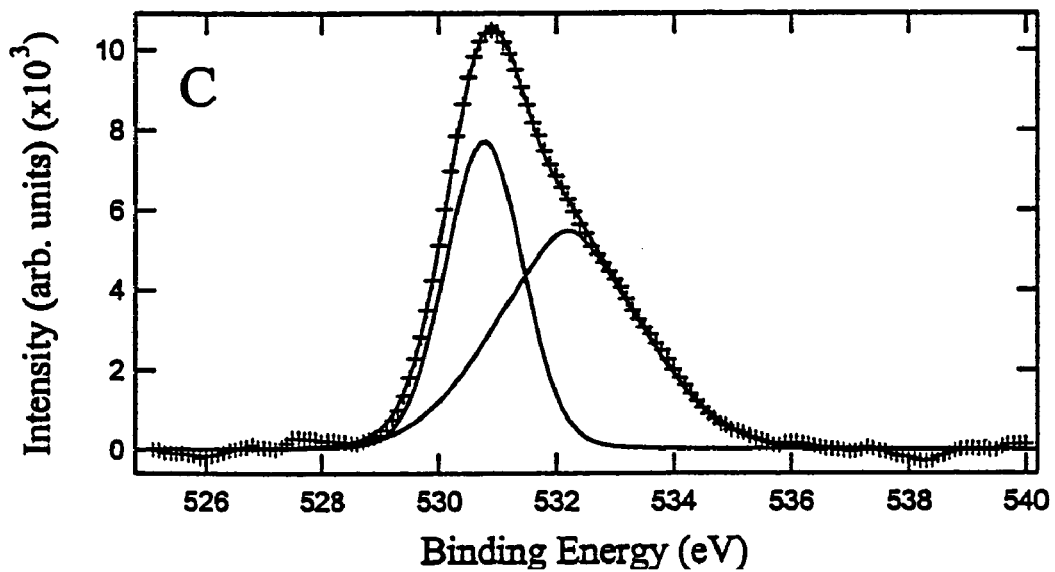

FIGS. 21A, 21B, and 21C show the XPS spectra of O 1s of bare ITO (FIG. 21A), an adlayer of 12-phosphonododecanoic acid on ITO (FIG. 21B), and an adlayer of 1-hexadecanethiol on ITO (FIG. 21C). The raw data is plotted with markers (+) and the individual and total 90/10 Gaussian/Lorenztian fits are shown with a solid line. The two components of the O 1s spectra for bare ITO occur at 530.7 and 531.7 eV, which correspond to indium oxide and tin oxide species, respectively as shown in FIG. 21A. Yan C.; Zharnikov, M.; Golzhauser, A.; Grunze, M. *Langmuir* 2000, 16 6208–6215. The ratio between In—O and Sn—O is 1.7 for bare ITO and shifts to 1.6 and 1.3 for 1-hexadecanethiol and 12-phosphonododecanoic acid on ITO, respectively, according to the data shown in FIGS. 21B and 21C. The peak positions for both of the monolayer structures, that is, 1-hexadecanethiol and 12-phosphonododecanoic acid on ITO, are 530.8 and 532.2 eV. The O 1s spectra of the other samples did not show any difference in the peak position or peak area ratio relative to bare ITO.

Figure 22A:
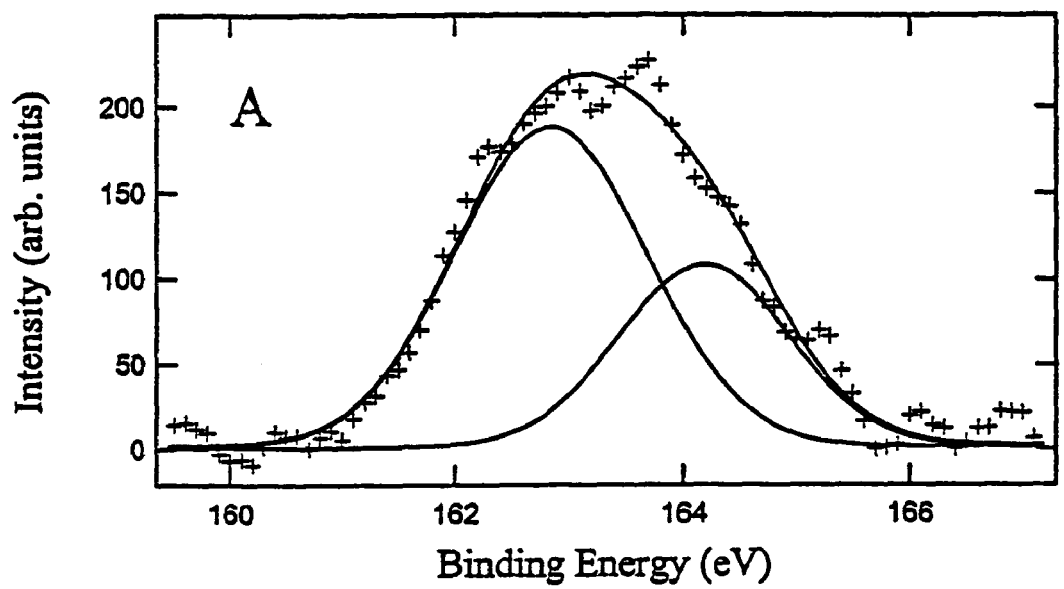
FIGS. 22A and 22B are the sulfur $2p_{3/2,1/2}$ XPS spectra of an adlayer of 1-hexadecanethiol on ITO (FIG. 22A) and a partial adlayer of dodecanethiol on ITO (FIG. 22B)
Figure 22B:
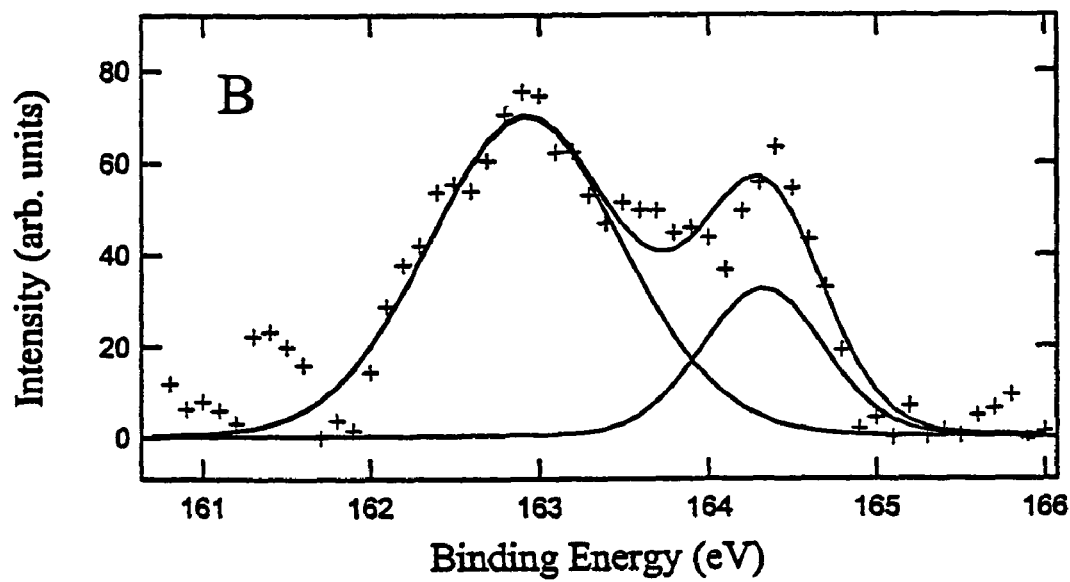

FIGS. 22A and 22B show the sulfur $2p_{3/2,1/2}$ XPS spectra of an adlayer of 1-hexadecanethiol on ITO (FIG. 22A) and a partial adlayer of dodecanethiol on ITO (FIG. 22B). The raw data is shown with markers (+) and the individual and total 90/10 Gaussian/Lorenztian fits are shown in a solid line. The peaks occur at 162.8 and 164.2 eV for 1-hexadecanethiol on ITO and at 162.9 and 164.3 eV for dodecanethiol on ITO. There were no observable peaks for octanethiol on ITO (data not shown). The overall peak intensities for dodecanethiol and octanethiol on ITO are 90 and 0% of the intensity of sulfur $2p_{3/2,1/2}$ relative to 1-hexadecanethiol on ITO, respectively. The peak positions for 1-hexadecanethiol and dodecanethiol are characteristic of a thiolate species of the alkane thiols. Yan C.; Zharnikov, M.; Golzhauser, A.; Grunze, M. *Langmuir* 2000, 16 6208–6215. Bain, C.; Biebuyck, H.; Witesides, G. *Langmuir* 1989, 5 723–727.

Figure 23:
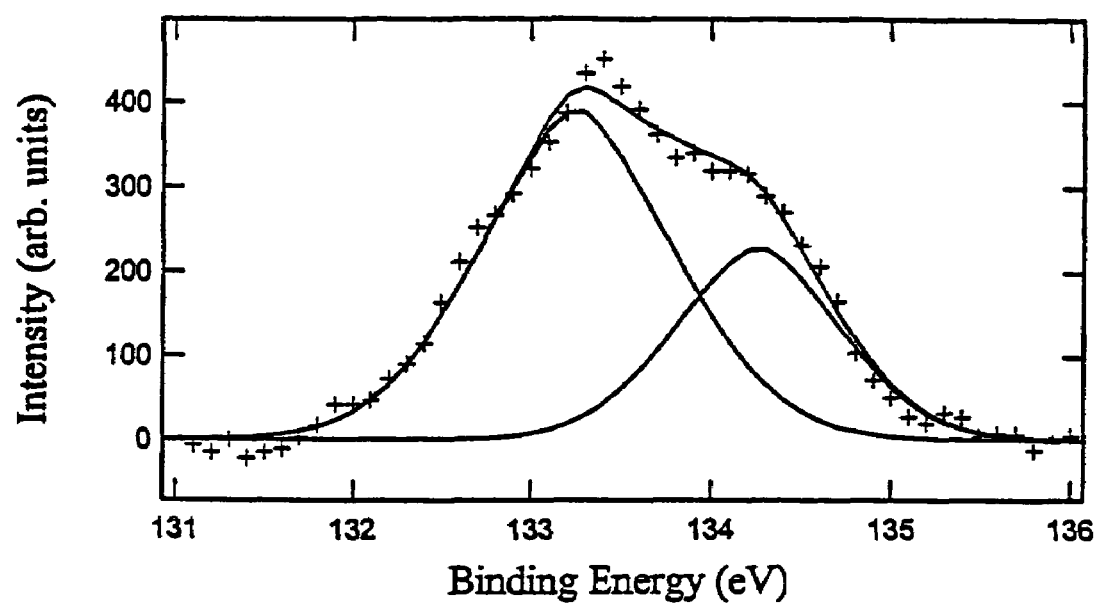
FIG. 23 is a spectra of the phosphorous $2p_{3/2,1/2}$ signals at 133.2 and 134.3 eV, respectively from an adlayer of 12-phosphonododecanoic acid (deposited from 50/50 (v/v) DMSO/18 MΩ·cm $H_2O$) on ITO.

FIG. 23 shows the phosphorous $2p_{3/2,1/2}$ signals at 133.2 and 134.3 eV, respectively from an adlayer of 12-phosphonododecanoic acid (deposited from 50/50 (v/v) DMSO/18 MΩ·cm H$_2$O) on ITO. The raw data is shown by markers (+), and the individual and total 90/10 Gaussian/Lorenztian fitted lines are shown in a solid line. The peak positions correspond to a fully deprotonated phosphonate group ($PO_3^{2-}$). Kohli, P.; Blanchard, G. *Langmuir* 2000, 16, 8518–8524. Seip, C.; Talham, D. *Materials Research Bulletin* 1999, 34 437–445. Petruska, M.; Ganucci, G.; Talham, D. *Chemistry of Materials* 1998, 10 177–189. The corresponding phosphorous $2p_{3/2,1/2}$ peak intensities are 30% lower for the partial adlayer formed from DMSO (data not shown).

Sequential Electrode Immersions.

The stability of the adlayer structures of 1-hexadecanethiol and 12-phosphononododecanoic acid on ITO were investigated through exchange reactions. The ITO electrodes that were first immersed in 10 mM 12-phosphonododecanoic acid in 50/50 (v/v) DMSO/18 MΩ·cm H$_2$O (16 hours) were then immersed in 1-hexadecanethiol (16 hours) and vice versa. The resulting spectra showed that neither of the adlayers were displaced by the other molecule (data not shown).

FTIR reflectance measurements show that indium tin oxide (ITO) and fluorine-doped tin oxide (SFO) electrodes are highly reflective in the mid-IR region (650–4000 cm$^{-1}$) and that the reflectance is a function of incident angle, polarization, and wavenumber. This high reflectivity allows reflectance FTIR spectroscopy to probe structures on the surfaces of these two electrodes. The combination of reflectance FTIR spectroscopy and X-ray photoelectron spectroscopy provide evidence that chemisorbed adlayers of alkyl thiolates and phosphonates form on ITO and SFO films.

Reflectance FTIR and XPS show that a close-packed, stable monolayer structure of 1-hexadecanethiol is formed on ITO and SFO electrodes through a thiolate interaction with the metal atoms of the surface. The XPS results agree with those of a previous report (Yan C.; Zharnikov, M.; Golzhauser, A.; Grunze, M. *Langmuir* 2000, 16 6208–6215.) and the optical spectroscopy lends further support to the hypothesis that the thiolate film is well-ordered. Variable angle reflectance FTIR spectroscopy demonstrates an ordered monolayer structure on both ITO and SFO electrodes by the decrease of the frequency of the C—H methylene stretches relative to neat 1-hexadecanethiol and by their signal intensities. This frequency decrease is the result of packing interactions between neighboring molecules, as the close-packed monolayer is formed, which was successfully modeled using periodic boundary conditions. The position of the sulfur $2p_{3/2,1/2}$ signal and the attenuation of In $3d_{5/2,3/2}$ and Sn $3d_{5/2,3/2}$ and the increase in Carbon 1s XPS signals relative to bare ITO demonstrates the presence of a monolayer of 1-hexadecanethiol on ITO with a thiolate-metal interaction. Yan, C.; Zharnikov, M.; Golzhauser, A.; Grunze, M. *Langmuir* 2000, 16, 6208–6215. Bain, C.; Biebuyck, H.; Witesides, G. *Langmuir* 1989, 5, 723–727.

The formation of a monolayer of 1-hexadecanethiol on either ITO or SFO is enthalpically driven by the thiolate—metal (e.g., In or Sn) interaction and the interaction between neighboring alkane chains. As observed previously on Au surfaces (Ulman, A. *Chemical Reviews* 1996, 96, 1533–1554. Lavrich, D.; Wetterer, S.; Bernasek, S.; Scoles, G. *Journal of Physical Chemistry B* 1998, 102, 3456–3465.), the chain length dependence of film stability is demonstrated experimentally here by the formation of a partial monolayer of dodecanethiol and the lack of any monolayer structure of octanethiol. Evidence for the relative coverage as a function of alkane chain length may be found in the relative attenuation of the indium $3d_{5/2,3/2}$ and tin $3d_{5/2,3/2}$ XPS signals and the small or absent sulfur $2p_{3/2,1/2}$ signal for dodecanethiol or octanethiol, respectively.

12-Phosphonododecanoic acid also formed a close-packed, stable monolayer structure on ITO as shown by reflectance FTIR and XPS through the interaction between fully oxidized phosphonate groups ($PO_3^{2-}$) and metal atoms of the surface when deposited from 50/50 (v/v) DMSO/18 MΩ·cm H$_2$O. The position of the XPS phosphorous $2p_{3/2,1/2}$ peak shows that the phosphonate group is apparently in the $PO_3^{2-}$ form in this monolayer structure and that only a partial monolayer is formed from DMSO by the relatively smaller attenuation of the In $3d_{5/2,3/2}$ and Sn $3d_{5/2,3/2}$ XPS signals and decreased Carbon 1s and phosphorous $2p_{3/2,1/2}$ signals. Kohli, P.; Blanchard, G. *Langmuir* 2000, 16, 8518–8524. Seip, C.; Talham, D. *Materials Research Bulletin* 1999, 34 437–445. Petruska, M.; Ganucci, G.; Talham, D. *Chemistry of Materials* 1998, 10 177–189. Therefore, the results may demonstrate that monolayer formation of 12-phosphonododecanoic acid may be highly dependent upon the deposition parameters. The signal frequencies of the carbonyl and methylene C—H stretches for the monolayer structure of 12-phosphonododecanoic acid when deposited from 50/50 (v/v) DMSO/18 MΩ·cm H$_2$O appear to be intermediate the solid and solution values of these frequencies. Thus, the reflectance FTIR spectroscopy appears to demonstrate a close-packed, ordered monolayer structure of 12-phosphonododecanoic acid when deposited from 50/50 (v/v) DMSO/18 MΩ·cm H$_2$O. The decrease in frequencies of these vibrations as compared to solution values may be the result of packing interactions between neighboring chains in the monolayer. However, the increase in the methylene C—H symmetric stretch relative to the solution values may indicate that a disordered structure could have been formed when 12-phosphonododecanoic acid was deposited from DMSO on ITO. The carboxylic acid of 12-phosphonododecanoic is protonated in the monolayer structure formed from 50/50 (v/v) DMSO/18 MΩ·cm H$_2$O based on literature values of carboxylate stretching frequencies of carboxylate groups interacting with oxidized aluminum surfaces. Allara, D.; Nuzzo, R. *Langmuir* 1985, 1, 52–66. For example, n-alkanoic acids interating with oxidized aluminum surfaces in the carboxylate form experimentally showed frequencies at 1608 cm$^{-1}$ on metal oxide surfaces involving carbon and oxygen. The lack of a carbonyl frequency in the deposited DMSO suggests that the transition dipole moment of the carbonyl group may be parallel to the surface.

Many of the conditions used did not appear to lead to formation of ordered monolayers on the two metal oxides studied. Based on the reflectance FTIR and XPS data signal intensities, no monolayers were formed by sodium dodecyl sulfate on ITO or SFO electrodes or by 12-phosphonododecanoic acid on SFO by any of the deposition solvent systems used. All of these samples showed no or low intensity signals in the reflectance FTIR spectra and little if any attenuation of indium 3d$_{5/2,3/2}$ and tin 3d$_{5/2,3/2}$ or an increase in carbon 1s XPS signals (or presence of other elements of the monolayer material).

Therefore, variable angle reflectance FTIR spectroscopy may be effective in characterizing adlayers on both ITO and SFO electrodes due the high reflectivity in the mid-IR. Reflectance FTIR and XPS indicated that monolayers of 1-hexadecanethiol on ITO and SFO may form through a thiolate—metal interaction. A monolayer of 12-phosphonododecanoic acid was observed by reflectance FTIR and XPS on ITO which may indicate a phosphonate—indium interaction. The enthalpic factors governing these monolayer formations may arise from the interaction with the metal atoms of the surface by one end of the molecule forming the monolayer and by hydrophobic (packing) interactions, which are affected by chain length.

The Effect of Surface Adlayers on the Plasmon Resonance Frequency

Figure 24A:
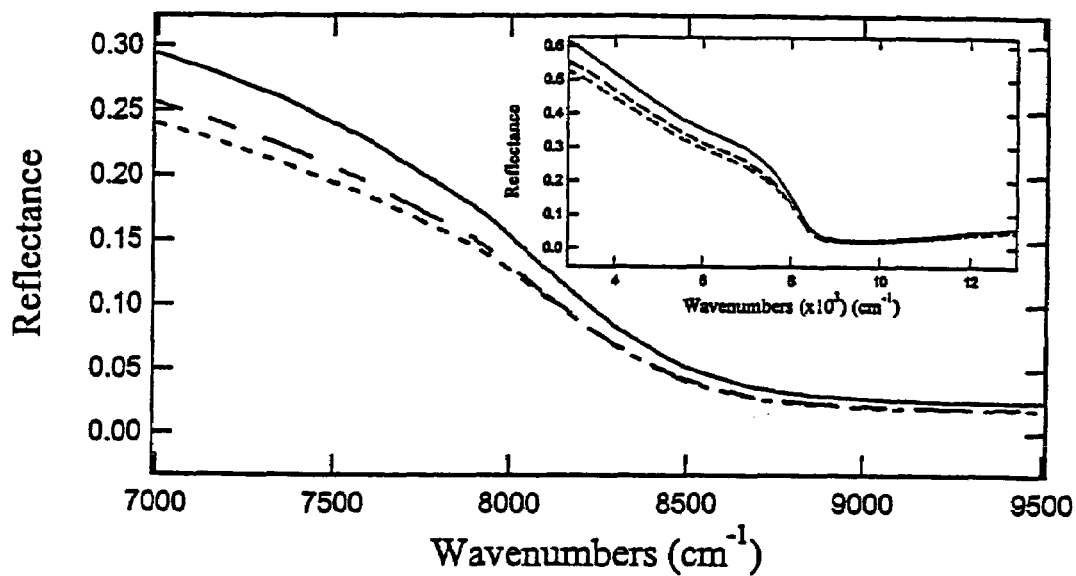
FIG. 24A is an FTIR spectra using an air/adlayer/ITO glass geometry.
Figure 24B:
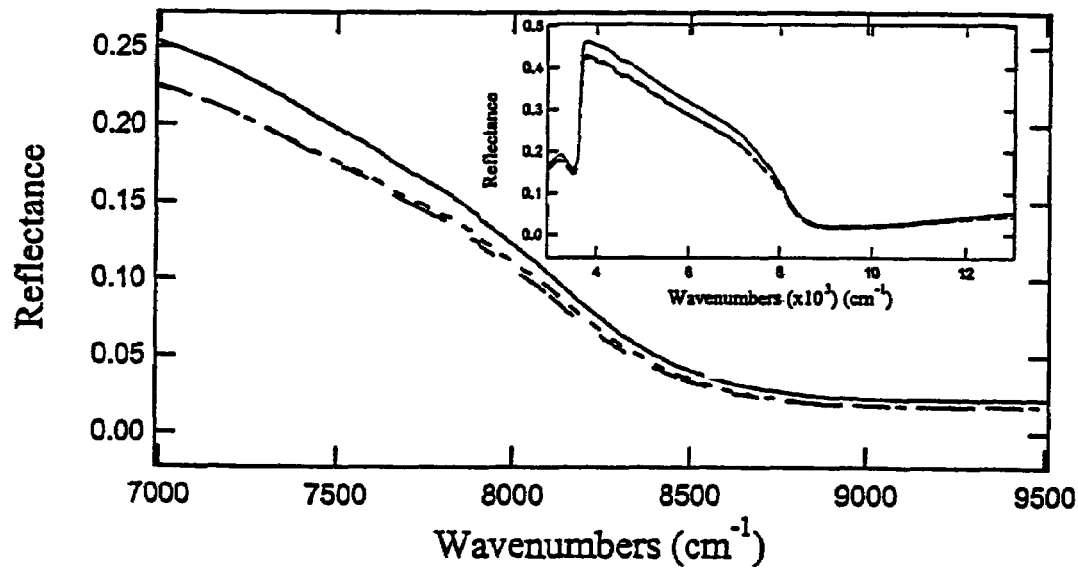
FIG. 24B is an FTIR spectra using an air/glass/ITO adlayer geometry.

FIGS. 24A and 24B illustrate the effect of an adlayer on the reflectivity and plasmon frequency of ITO in the mid- and near-IR region at an incident angle of 60 degrees with p-polarized radiation. Spectra are shown for bare ITO (solid line), an adlayer of 12-phosphonododecanoic acid on ITO (- - spectrum), and an adlayer of 1-hexadecanethiol on ITO (-- -- spectrum). The experimental reflectance FTIR spectra in FIG. 24A were recorded in an air/adlayer/ITO/glass sampling geometry. An air/glass/ITO/adlayer sampling geometry was used to measure the reflectance FTIR spectra in FIG. 24B. An adlayer of 12-phosphonododecanoic acid or 1-hexadecanethiol on ITO were used to illustrate the effect of adlayer formation on the optical properties of ITO. In both of the sampling geometries (FIGS. 24A and 24B), the reflectance and observed plasmon frequency of ITO decreases due to the presence of either of the adlayers relative to bare ITO. Therefore, both the shift in the plasmon frequency in the near-IR and the change in reflectivity in the mid-IR of ITO due to adlayer formation may be utilized to observe binding events such as the formation of an adlayer on ITO.

EXAMPLE 4

FTIR Plasmon Resonance Modulation

In addition to the reflected light source for obtaining reflectance FTIR spectra, a second modulating light source may be used to shine on an optical layer. Such a light source may modulate the plasmon bands obtained and increase the sensitivity of the detection of adlayers.

Figure 25A:
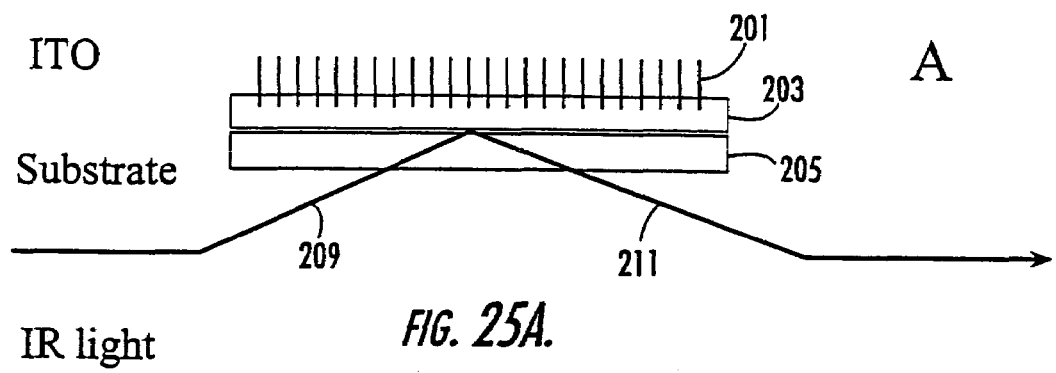
FIGS. 25A and 25B are a schematic drawings of embodiments of the invention using a mid-infrared or near-infrared interferometric spectrometer without a second modulating light source.
Figure 25B:
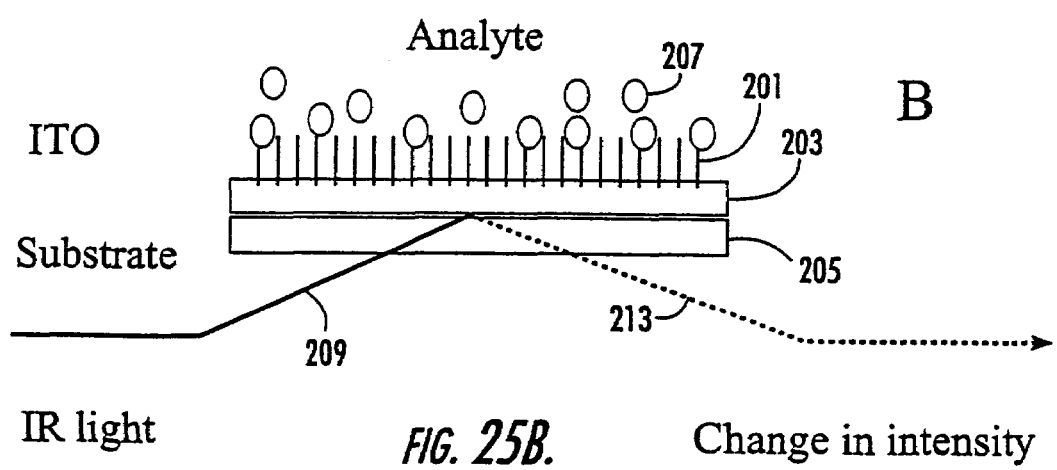

FIGS. 25A and 25B illustrate embodiments of the invention using a mid-infrared or near-infrared interferometric spectrometer without a second modulating light source. In FIG. 25A, a first member 201 of a specific binding pair is on the ITO optical layer 203. Impinging light 209 shines through a transparent substrate layer 205 onto the ITO optical layer 203. The resulting reflected light 211 can be detected as a plasmon spectra characteristic of the ITO optical layer 203. Preferably, the impinging light 209 has an energy higher than the band gap of the ITO optical layer 203.

In FIG. 25B, a second member 207 of the specific binding pair binds with the first member 201. As a result, the optical properties of the ITO optical layer 203 are altered. The optical change of the ITO optical layer 203 may be observed by the change in intensity in the reflected light 213 when compared to the reflected light 211 in FIG. 25A where no binding has occurred on the ITO optical layer 203.

FIGS. 26A and 26B illustrate embodiments of the invention using a mid-infrared or near-infrared interferometric spectrometer having a second modulating light source. In FIG. 26A, a first member 201 of a specific binding pair is on the ITO optical layer 203. Ultraviolet light 219 shines on the optical layer 203. Impinging light 209 shines through a transparent substrate layer 205 onto the ITO optical layer 203. The resulting reflected light 215 has a modulated intensity due to the application of ultraviolet light 219, which results in a ultraviolet light modulated plasmon spectra characteristic of the ITO optical layer 203. Preferably, the ultraviolet light 219 has an energy higher than the band gap of the ITO optical layer 203.

In FIG. 26B, a second member 207 of the specific binding pair binds with the first member 201. As a result, the optical properties of the ITO optical layer 203 are altered in addition to the modulation due to the ultraviolet light 215. The optical change of the ITO optical layer 203 may be observed by the change in intensity in the reflected light 217 when compared to the reflected light 211 in FIG. 26A where no binding has occurred on the ITO optical layer 203.

The modulation of the surface plasmon spectra by a second light source such as the ultraviolet light 215 shown in FIG. 26B may increase the ability to detect changes due to surface binding. Other frequencies of light may be used. Preferably the light source produces light having an energy higher than the band gap of the optical layer.

In the drawings and specification, there have been disclosed typical preferred embodiments of the invention and, although specific terms are employed, they are used in a generic and descriptive sense only and not for purposes of limitation, the scope of the invention being set forth in the following claims. Moreover, laser and detection configurations and techniques known to those of skill in the art may be used to accomplish the functions and features of the embodiments described herein.

What is claimed is:

1. A device for detecting a member of a specific binding pair in a sample comprising:
   a substrate;
   a variable charge density layer having a surface adjacent to the substrate and a surface remote from the substrate;
   a first member of the specific binding pair on the variable charge density layer surface remote from the substrate, wherein the first member interacts with a second member of the specific binding pair present in a sample; and the variable charge density layer having a charge carrier density that can be changed by the application of light and/or an electric field, so that a plasmon band is detected by a reflected light source impinging on the variable charge carrier density layer.

2. The device according to claim 1, the plasmon band has a wave number between about 2,000 to about 20,000 cm$^{-1}$.

3. The device according to claim 1, wherein the plasmon band has a wave number between about 2,000 and about 14,000 cm$^{-1}$.

4. The device according to claim 1, wherein the substrate is transparent.

5. The device according to claim 1, wherein the substrate is nontransparent.

6. The device according to claim 1, wherein shining a second light source on the variable charge carrier density layer produces a modulation of a plasmon band measured by the reflected light source impinging upon the variable charge density layer.

7. The device according to claim 1, wherein the variable charge density layer comprises a metal oxide.

8. The device according to claim 1, wherein the variable charge density layer comprises a metal chalcogenide.

9. The device according to claim 1, wherein the variable charge density layer comprises a non-degenerate semiconductor.

10. The device according to claim 1, wherein the variable charge density layer comprises a degenerate semiconductor.

11. The device according to claim 1, wherein the variable charge density layer comprises a conducting metal oxide or metal chalcogenide that is an infrared light reflector and transparent to visible light.

12. The device according to claim 1, wherein the variable charge density layer comprises at least one of indium tin oxide, fluorine-doped tin oxide, iridium oxide, ruthenium oxide, cadmium oxide, yttrium oxide, scandium oxide, yttrium tin oxide, and scandium tin oxide.

13. The device according to claim 1, wherein the first member is a monolayer on the surface of the variable charge density layer remote from the substrate.

14. The device according to claim 1, wherein the reflected light source comprises an infrared polarized light source.

15. A device for detecting a member of a specific binding pair in a sample comprising:
    a substrate;
    a semiconductor layer having a plasmon band and a surface adjacent the substrate and a surface remote from the substrate; and
    a first member of a specific binding pair on the surface of the semiconductor layer remote from the substrate, wherein the first member interacts with a second member of the specific binding pair present in a sample.

16. The device according to claim 15, wherein the plasmon band has a wave number between about 2,000 to about 20,000 cm$^{-1}$.

17. The device according to claim 15, wherein the plasmon band has a wave number between about 2,000 and about 14,000 cm$^{-1}$.

18. The device according to claim 15, wherein the substrate is transparent.

19. The device according to claim 15, wherein the substrate is nontransparent.

20. The device according to claim 15, wherein the semiconductor layer comprises a metal oxide.

21. The device according to claim 15, wherein the semiconductor layer comprises a degenerate semiconductor.

22. The device according to claim 15, wherein the semiconductor layer comprises a non-degenerate semiconductor.

23. The device according to claim 15, wherein the semiconductor layer comprises a conducting metal oxide or metal chalcogenide that is an infrared light reflector and transparent to visible light.

24. The device according to claim 15, wherein the semiconductor layer comprises at least one of indium tin oxide, fluorine-doped tin oxide, iridium oxide, ruthenium oxide, cadmium oxide, yttrium oxide, scandium oxide, yttrium tin oxide, and scandium tin oxide.

25. The device according to claim 15, wherein the first member of the specific binding pair is a monolayer on the surface of the semiconductor layer remote from the substrate.

26. The device according to claim 15, wherein a reflected light source produces the plasmon band.

27. The device according to claim 26, wherein shining a second light source on the semiconductor layer produces a modulation of a plasmon band measured by the reflected light source impinging upon the semiconductor layer.

28. The device according to claim 15, wherein the semiconductor layer has a variable charge carrier density.

29. A system for detecting a member of a specific binding pair in a sample comprising:
    a substrate;
    a variable charge density layer having a surface adjacent the substrate and a surface remote from the substrate; and
    a first member of the specific binding pair on the variable charge density layer surface remote from the substrate, wherein the first member interacts with a second member of the specific binding pair present in a sample;
    a means for changing the variable charge density of the variable charge density layer for producing a plasmon band;
    a means for detecting the plasmon band from the variable charge density layer.

30. The system according to claim 29, wherein the means for changing the variable charge density of the variable charge density layer comprises a generator configured to apply light.

31. The system according to claim 29, wherein the means for changing the charge density of the variable charge density layer comprises a generator configured to apply an electric field.

32. The system according to claim 29, wherein the means for changing the variable charge density comprises a reflected light source positioned to impinge on the variable charge density layer for producing a plasmon band.

33. The system according to claim 30, wherein the means for detecting the plasmon band comprises a detector positioned to detect light reflected from the variable charge density layer.

34. The system according to claim 29, wherein the plasmon band has a wave number between about 2,000 to about 20,000 cm$^{-1}$.

35. The system according to claim 29, wherein the plasmon band has a wave number between about 2,000 and about 14,000 cm$^{-1}$.

36. The system according to claim 29, wherein the substrate is transparent.

37. The system according to claim 29, wherein the substrate is nontransparent.

38. The system according to claim 29, wherein shining a second light source on the variable charge carrier density layer produces a modulation of a plasmon band measured by the reflected light source impinging upon the variable charge carrier density layer.

39. The system according to claim 29, wherein the variable charge carrier density layer comprises a metal oxide.

40. The system according to claim 29, wherein the variable charge carrier density layer comprises a metal chalcogenide.

41. The system according to claim 29, wherein the variable charge carrier density layer comprises a degenerate semiconductor.

42. The system according to claim 29, wherein the variable charge carrier density layer comprises a non-degenerate semiconductor.

43. The system according to claim 29, wherein the variable charge carrier density layer comprises a conducting metal oxide or metal chalcogenide that is an infrared light reflector and transparent to visible light.

44. The system according to claim 29, wherein the variable charge carrier density layer comprises at least one of indium tin oxide, fluorine-doped tin oxide, iridium oxide, ruthenium oxide, cadmium oxide, yttrium oxide, scandium oxide, yttrium tin oxide, and scandium tin oxide.

45. The system according to claim 29, wherein the first member is a monolayer on the surface of the variable charge density layer remote from the substrate.

46. The system according to claim 29, wherein the reflected light source comprises an infrared polarized light source.

47. The system according to claim 29, wherein the means for detecting a change in plasmon band frequency comprises a means for detecting performed at a fixed angle.

48. A method for detecting a member of a specific binding pair in a sample comprising:
altering the charge carrier density of a variable charge density layer in response to a binding event.

49. The method of claim 48, wherein altering the charge carrier density comprises altering the plasmon of the variable charge density layer.

50. The method of claim 48, further comprising:
detecting the plasmon band of the variable charge density layer.

51. The method of claim 48, further comprising:
detecting a change in the electromagnetic field of the variable charge density layer.

52. The method of claim 48, further comprising:
applying light to the variable charge density layer to modulate the plasmon band of the variable charge density layer.

53. The method of claim 48, further comprising:
applying an electric field to the variable charge density layer to modulate the plasmon band of the variable charge density layer.

54. The method of claim 48, further comprising:
modulating the plasmon band of the variable charge density layer.

55. A method for detecting a member of a specific binding pair in a sample comprising:
detecting a first plasmon band measurement from a reflected light source on an optical layer having a first member of a specific binding pair attached thereto;
placing a sample in contact with the first member of the specific binding pair;
detecting a second plasmon band measurement from the reflected light source on the optical layer; and
if a plasmon frequency shift in the first and second plasmon band measurements is detected to indicate binding, determining that the sample comprises a second member of the specific binding pair.

56. The method according to claim 55, wherein the first and second plasmon band measurements have wave numbers between about 2,000 to about 20,000 cm$^{-1}$.

57. The method according to claim 55, wherein the first and second plasmon band measurements have wave numbers between about 2,000 to about 14,000 cm$^{-1}$.

58. The method according to claim 55, further comprising:
shining a second light source on the optical layer during the detecting first and second plasmon band measurements steps, wherein the second light source modulates the first and second plasmon band measurements.

59. The method according to claim 55, wherein the optical layer comprises a metal oxide.

60. The method according to claim 55, wherein the optical layer comprises a metal chalcogenide.

61. The method according to claim 55, wherein the optical layer comprises a semiconductor.

62. The method according to claim 55, wherein the optical layer comprises a degenerate semiconductor.

63. The method according to claim 55, wherein the optical layer comprises a non-degenerate semiconductor.

64. The method according to claim 55, wherein the optical layer comprises a conducting metal oxide or metal chalcogenide that is an infrared light reflector and transparent to visible light.

65. The method according to claim 55, wherein the optical layer comprises at least one of indium tin oxide, fluorine-doped tin oxide, iridium oxide, ruthenium oxide, cadmium oxide, yttrium oxide, scandium oxide, yttrium tin oxide, and scandium tin oxide.

66. The method according to claim 55, wherein the interactive layer is a monolayer on the optical layer.

67. The method according to claim 55, wherein the reflected light source is an infrared polarized light source.

68. The method according to claim 55, wherein the detecting a change in plasmon band frequency is performed at a fixed angle.

69. A method for detecting a member of a specific binding pair in a sample comprising:
detecting a first plasmon band measurement from a reflected first light source on an optical layer having a first member of a specific binding pair attached thereto;
placing in contact with the first member of the specific binding pair;
detecting a second plasmon band measurement from the reflected first light source on the optical layer; and
shining a second light source on the optical layer to modulate the first and second plasmon band measurements.

70. The method of claim 69, further comprising:
if a plasmon frequency shift in the first and second plasmon band measurements is detected to indicate binding, determining that the sample comprises a second member of the specific binding pair.

71. The method of claim 69, wherein the first and second plasmon band measurements have wave numbers between about 2,000 to about 20,000 cm$^{-1}$.

72. The method of claim 69, wherein the first and second plasmon band measurements have wave numbers between about 2,000 to about 14,000 cm$^{-1}$.

73. The method of claim 69, wherein the optical layer comprises a metal oxide.

74. The method of claim 69, wherein the optical layer comprises a metal chalcogenide.

75. The method of claim 69, wherein the optical layer comprises a semiconductor.

76. The method of claim 69, wherein the optical layer comprises a non-degenerate semiconductor.

77. The method of claim 69, wherein the optical layer comprises a degenerate semiconductor.

78. The method of claim 69, wherein the optical layer comprises a conducting metal oxide or metal chalcogenide that is an infrared light reflector and transparent to visible light.

79. The method of claim 69, wherein the optical layer comprises at least one of indium tin oxide, fluorine-doped tin oxide, iridium oxide, ruthenium oxide, cadmium oxide, yttrium oxide, scandium oxide, yttrium tin oxide, and scandium tin oxide.

80. The method of claim 69, wherein the interactive layer is a monolayer on the optical layer.

81. The method of claim 69, wherein the reflected light source is an infrared polarized light source.

* * * * *